(12) United States Patent
Walker et al.

(10) Patent No.: US 11,064,887 B1
(45) Date of Patent: Jul. 20, 2021

(54) INTERACTIVE ELECTRONIC TREATMENT ASSISTANCE FOR BENIGN PROSTATIC HYPERPLASIA AND ADVANCED PROSTATE CANCER

(71) Applicant: ROGUE MEDICAL SOLUTIONS, LLC, Eugene, OR (US)

(72) Inventors: Brady R. Walker, Eugene, OR (US); David S. DiMarco, Eugene, OR (US); Connie S. DiMarco, Eugene, OR (US)

(73) Assignee: Rogue Medical Solutions, LLC, Eugene, OR (US)

( * ) Notice: Subject to any disclaimer, the term of this patent is extended or adjusted under 35 U.S.C. 154(b) by 323 days.

(21) Appl. No.: 16/351,495

(22) Filed: Mar. 12, 2019

Related U.S. Application Data

(60) Provisional application No. 62/642,300, filed on Mar. 13, 2018.

(51) Int. Cl.
  *A61B 5/00* (2006.01)
  *G16H 40/67* (2018.01)
  *G16H 80/00* (2018.01)

(52) U.S. Cl.
  CPC .......... *A61B 5/0022* (2013.01); *A61B 5/6898* (2013.01); *G16H 40/67* (2018.01); *G16H 80/00* (2018.01)

(58) Field of Classification Search
  CPC combination set(s) only.
  See application file for complete search history.

(56) References Cited

U.S. PATENT DOCUMENTS

2016/0081575 A1* 3/2016 Wu ................... G16H 20/17
600/301

* cited by examiner

*Primary Examiner* — Nabil H Syed
*Assistant Examiner* — Cal J Eustaquio
(74) *Attorney, Agent, or Firm* — Renaissance IP Law Group, LLP; David A. Crowther

(57) ABSTRACT

Computer-implemented methods for providing interactive electronic treatment assistance for benign prostatic hyperplasia and advanced prostate cancer are disclosed. The methods can include automatically sending, by a disease and disorder treatment device, an electronic pathway sign-up link to a smart mobile device. The method can include sending a plurality of inquiries about the BPH condition and/or the advanced prostate cancer condition, to the smart mobile device. The method can include receiving a plurality of patient responses from the smart mobile device. The method can include processing and storing the plurality of patient responses. The method can include providing, by the disease and disorder treatment device, patient education about various treatment therapies for advanced prostate cancer. The method can include automatically monitoring a patient having the advanced prostate cancer condition during the various treatment therapies. The method can include intervening with the various treatment therapies using the smart mobile device.

13 Claims, 24 Drawing Sheets

INTERACTIVE ELECTRONIC TREATMENT ASSISTANCE FOR BENIGN PROSTATIC HYPERPLASIA AND ADVANCED PROSTATE CANCER

RELATED APPLICATION DATA

This application claims the benefit of U.S. Provisional Application Ser. No. 62/642,300, filed on Mar. 13, 2018, the contents of which are hereby incorporated by reference.

TECHNICAL FIELD

This application pertains to the field of medicine, and more particularly, to methods and systems pertaining to interactive treatment assistance for benign prostatic hyperplasia (BPH) and advanced prostate cancer.

BACKGROUND

Benign prostatic hyperplasia (BPH) and advanced prostate cancer are common among the population at large, and cost significant health care dollars per year for treatment and diagnosis. The treatment processes can be prolonged with multiple office visits, trials of medications, testing, and advanced treatments. The processes can be arduous for patient and provider.

Accordingly, a need remains for improved methods and systems for interactively assisting patients in their treatment of these disorders and diseases. Embodiments of the inventive concept address these and other limitations in the prior art.

The foregoing and other features of the inventive concept will become more readily apparent from the following detailed description, which proceeds with reference to the accompanying drawings.

DETAILED DESCRIPTION OF THE EMBODIMENTS

Reference will now be made in detail to embodiments of the inventive concept, examples of which are illustrated in the accompanying drawings. The accompanying drawings are not necessarily drawn to scale. In the following detailed description, numerous specific details are set forth to enable a thorough understanding of the inventive concept. It should be understood, however, that persons having ordinary skill in the art may practice the inventive concept without these specific details. In other instances, well-known methods, procedures, components, circuits, and networks have not been described in detail so as not to unnecessarily obscure aspects of the embodiments.

It will be understood that, although the terms first, second, etc. may be used herein to describe various elements, these elements should not be limited by these terms. These terms are only used to distinguish one element from another. For example, a first interactive treatment could be termed a second interactive treatment, and, similarly, a second interactive treatment could be termed a first interactive treatment, without departing from the scope of the inventive concept.

It will be understood that when an element or layer is referred to as being "on," "coupled to," or "connected to" another element or layer, it can be directly on, directly coupled to or directly connected to the other element or layer, or intervening elements or layers may be present. In contrast, when an element is referred to as being "directly on," "directly coupled to," or "directly connected to" another element or layer, there are no intervening elements or layers present. Like numbers refer to like elements throughout. As used herein, the term "and/or" includes any and all combinations of one or more of the associated listed items.

The terminology used in the description of the inventive concept herein is for the purpose of describing particular embodiments only and is not intended to be limiting of the inventive concept. As used in the description of the inventive concept and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Figure 1A:
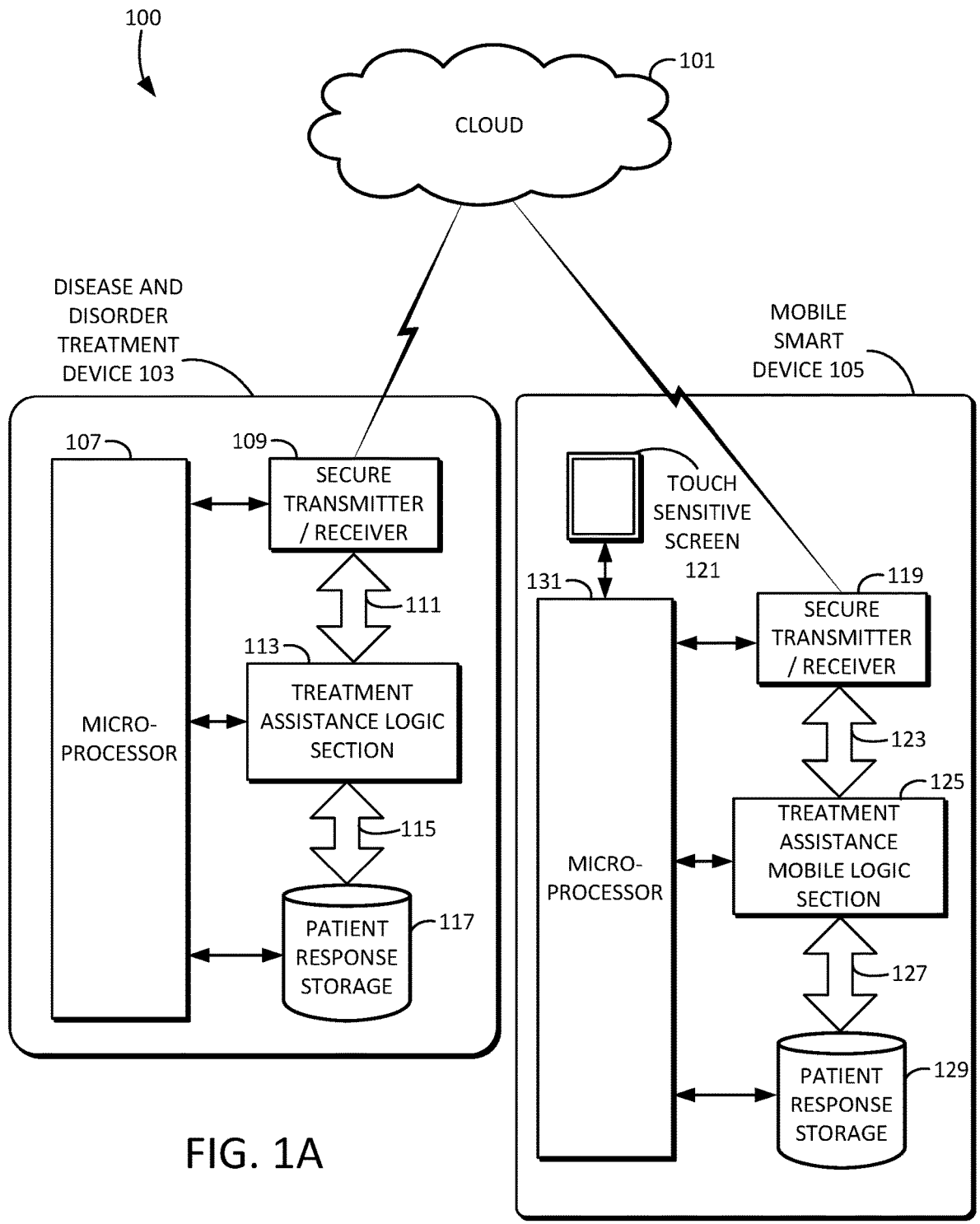
FIG. 1A illustrates a block diagram including a disease and disorder treatment device and a smart mobile device used in the assessment and treatment of diseases and disorders in accordance with various embodiments of the present inventive concept.
Figure 1B:
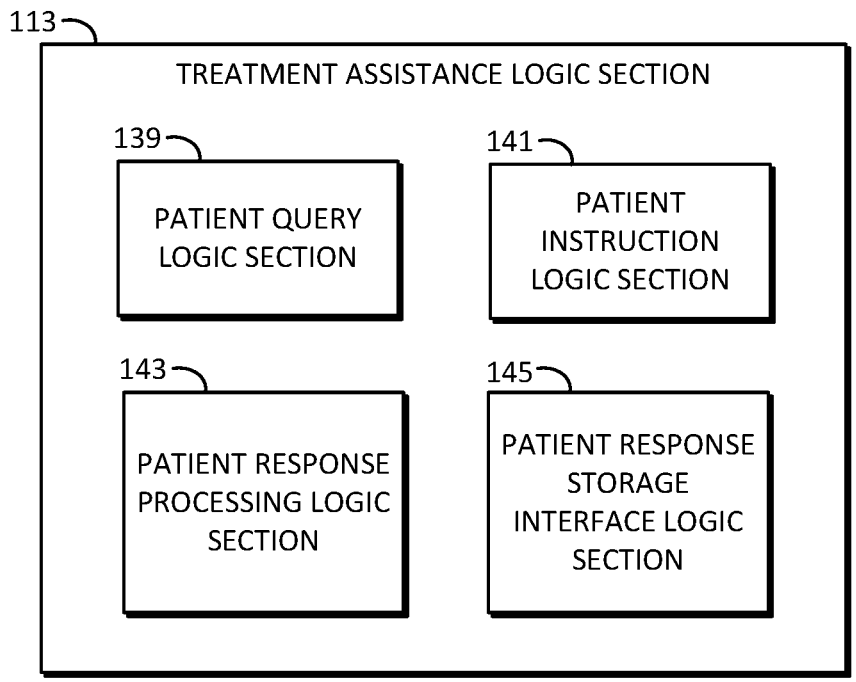
FIG. 1B illustrates a block diagram including details of the treatment assistance logic section in accordance with various embodiments of the present inventive concept.
Figure 1C:
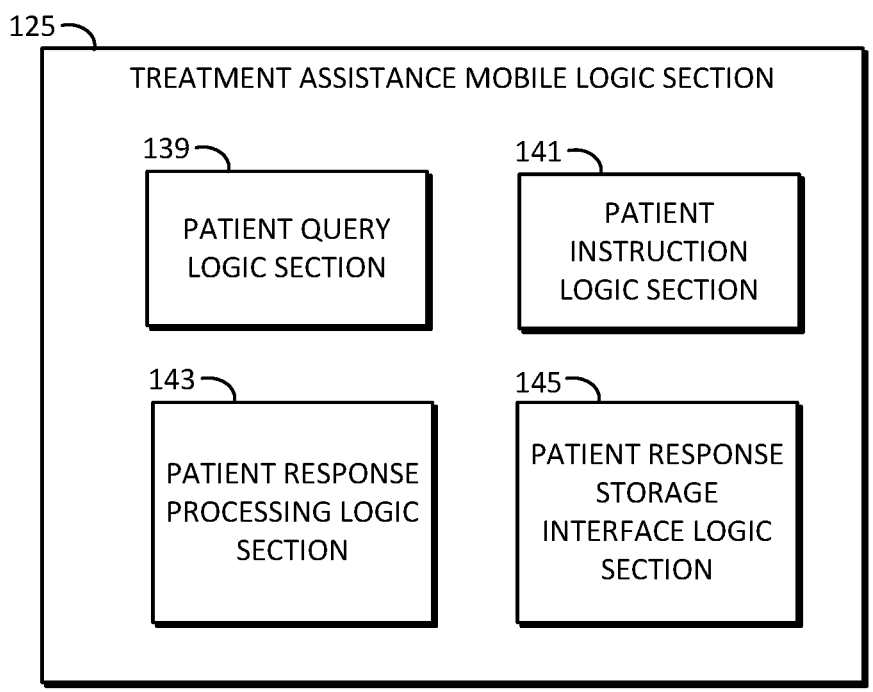
FIG. 1C illustrates a block diagram including details of the treatment assistance mobile logic section in accordance with various embodiments of the present inventive concept.

FIG. 1A illustrates a block diagram including system 100 having a disease and disorder treatment device 103 and a smart mobile device 105 used in the treatment of BPH and advanced prostate cancer in accordance with various embodiments of the present inventive concept. FIG. 1B illustrates a block diagram including details of a treatment assistance logic section 113 of FIG. 1A in accordance with various embodiments of the present inventive concept. FIG. 1C illustrates a block diagram including details of a treatment assistance mobile logic section 125 of FIG. 1A in accordance with various embodiments of the present inventive concept. FIGS. 1D through 1J illustrate a block and flow diagram showing a first interactive treatment assistance phase (i.e., phase 1) related to BPH in accordance with various embodiments of the present inventive concept. Reference is now made to FIGS. 1A through 1J.

As shown in FIG. 1A, a system 100 may include a disease and disorder treatment device 103 having a microprocessor 107, a secure transmitter/receiver 109 (i.e., transceiver), a treatment assistance logic section 113, and a patient response storage 117. The secure transmitter/receiver 109 may send and receive information to and from the cloud 101. The secure transmitter/receiver 109 can be communicatively coupled to the microprocessor 107 and/or to the treatment assistance logic section 113 via a bus 111. The treatment assistance logic section 113 can be communicatively coupled to the microprocessor 107 and/or to the patient response storage 117 via a bus 115. The patient response storage 117 can include volatile memory such as dynamic random access memory (DRAM), non-volatile memory such as a solid state storage device (SSD) or flash memory, or a hard disk drive such as a magnetic disk drive. The microprocessor 107 can assist in the execution of logic. The treatment assistance logic section 113 can process logic or provide assistance to the microprocessor 107 in the execution thereof.

The system 100 may further include a smart mobile device 105 such as a smart phone, smart tablet, or notebook computer. The smart mobile device 105 can include a microprocessor 131, a secure transmitter/receiver 119 (i.e., transceiver), a treatment assistance mobile logic section 125, a touch-sensitive screen 121, and a patient response storage 129. The secure transmitter/receiver 119 may send and receive information to and from the cloud 101. The secure transmitter/receiver 119 may send and receive information to and from the disease and disorder treatment device 103. The secure transmitter/receiver 119 can be communicatively coupled to the microprocessor 131 and/or to the treatment assistance mobile logic section 125 via a bus 123. The treatment assistance mobile logic section 125 can be communicatively coupled to the microprocessor 131 and/or to the patient response storage 129 via a bus 127. The patient response storage 129 can include volatile memory such as DRAM, non-volatile memory such as an SSD or flash memory, or a hard disk drive such as a magnetic disk drive. The microprocessor 131 can assist in the execution of logic. The treatment assistance mobile logic section 125 can process logic or provide assistance to the microprocessor 131 in the execution thereof.

FIG. 1B shows additional details of the treatment assistance logic section 113 including a patient query logic section 139, a patient instruction logic section 141, a patient response processing logic section 143, and a patient response storage interface logic section 145. FIG. 1C shows additional details of the treatment assistance mobile logic section 125 including a patient query logic section 139, a patient instruction logic section 141, a patient response processing logic section 143, and a patient response storage interface logic section 145. The functions performed by these various logic sections are explained in detail below.

A first phase in the automated interactive treatment assistance for BPH can include a number of steps. Referring to FIGS. 1D through 1J, a series of interactive steps can be carried out with the patient. Between each step, a patient response or affirmation can be received. The term "user affirmation" can refer, for example, to an acknowledgment from a patient. A "patient" is a patient that uses the system 100. The acknowledgement can include, for example, entering or typing in a string of text, clicking a button or icon displayed on a touch-sensitive electronic display using an instrument such as a computer mouse, selecting the button or icon on a touch-sensitive screen (e.g., 121 of FIG. 1A), making a swiping or other gesture on a touch-sensitive screen, audibly indicating an acknowledgment through a microphone, or the like. The button or icon can include a textual acceptance indicator such as an "OK," "Got it," "Agreed," or the like. Alternatively or in addition, the button or icon can include a graphical acceptance indicator such as a "thumbs up" sign. In some embodiments, a pure textual acceptance indicator can be used, a pure graphical acceptance indicator can be used, or a combination of text and graphical indicators can be used. In some embodiments, a scale from 1 to 10 can be used. The patient can be prevented from proceeding to the next step until the affirmation is received.

By signifying affirmation, the patient is more able and likely to retain the information presented, and more likely to comprehend it. In addition, the affirmation can be saved in a storage medium such as the patient response storage 117 of the treatment 103, and/or on the patient response storage 129 of the smart mobile device 105, as further described below, which can provide legal protection for the healthcare provider should the patient later claim that they were not made aware of the intricacies, risks, or procedures associated with the administered medical treatment.

Figure 1D:
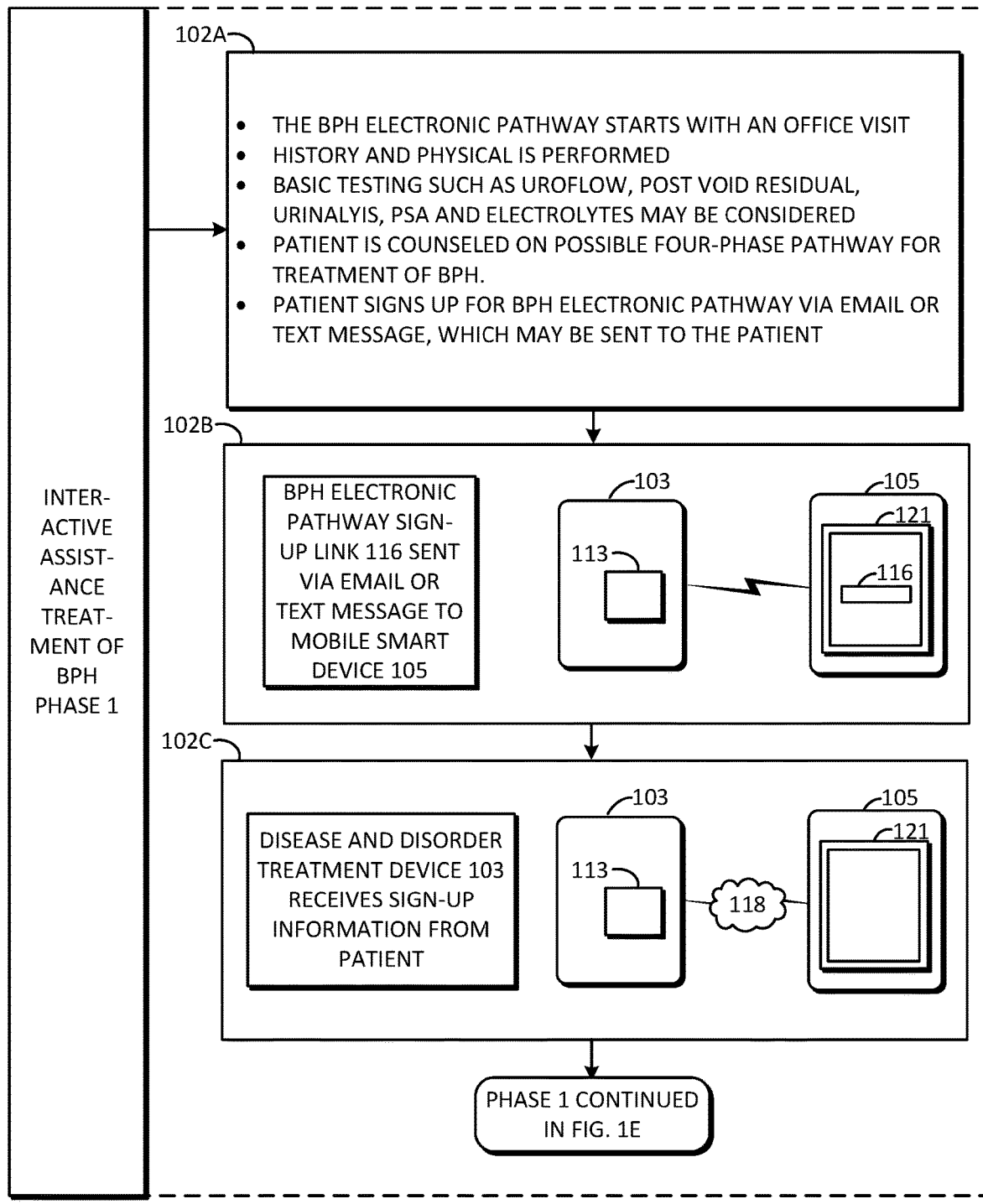
FIGS. 1D through 1J illustrate a block and flow diagram showing a first interactive treatment assistance phase related to BPH in accordance with various embodiments of the present inventive concept.
Figure 1E:
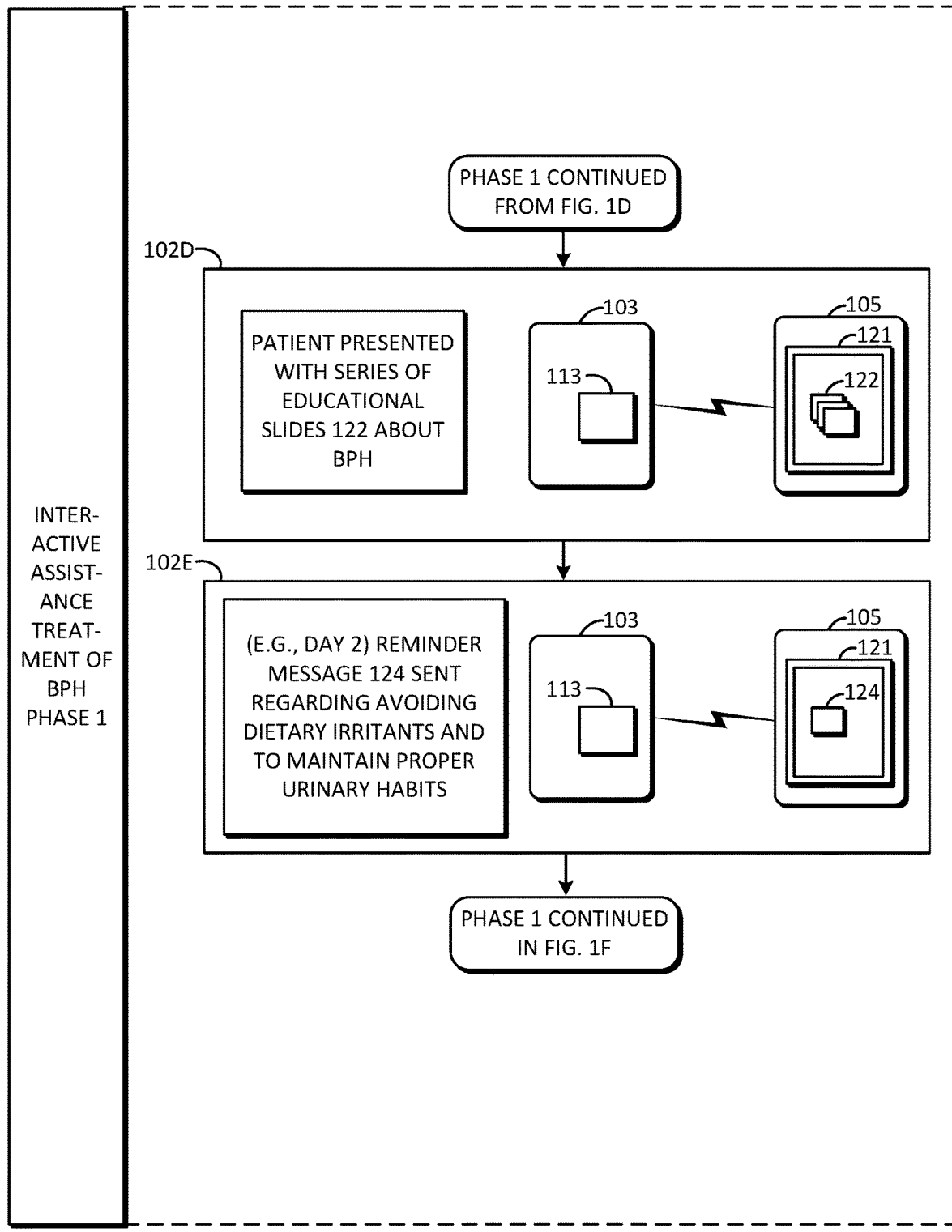
Figure 1F:
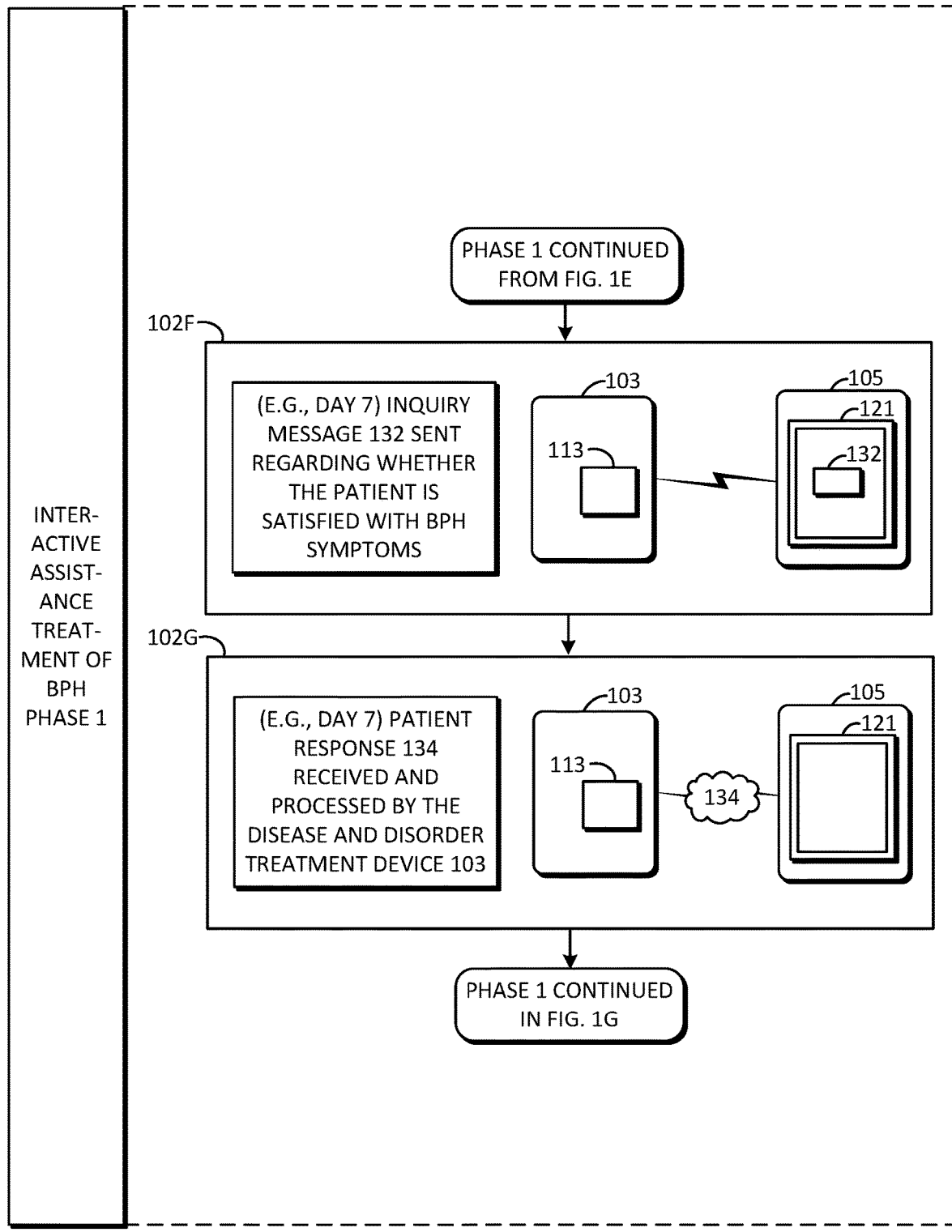
Figure 1G:
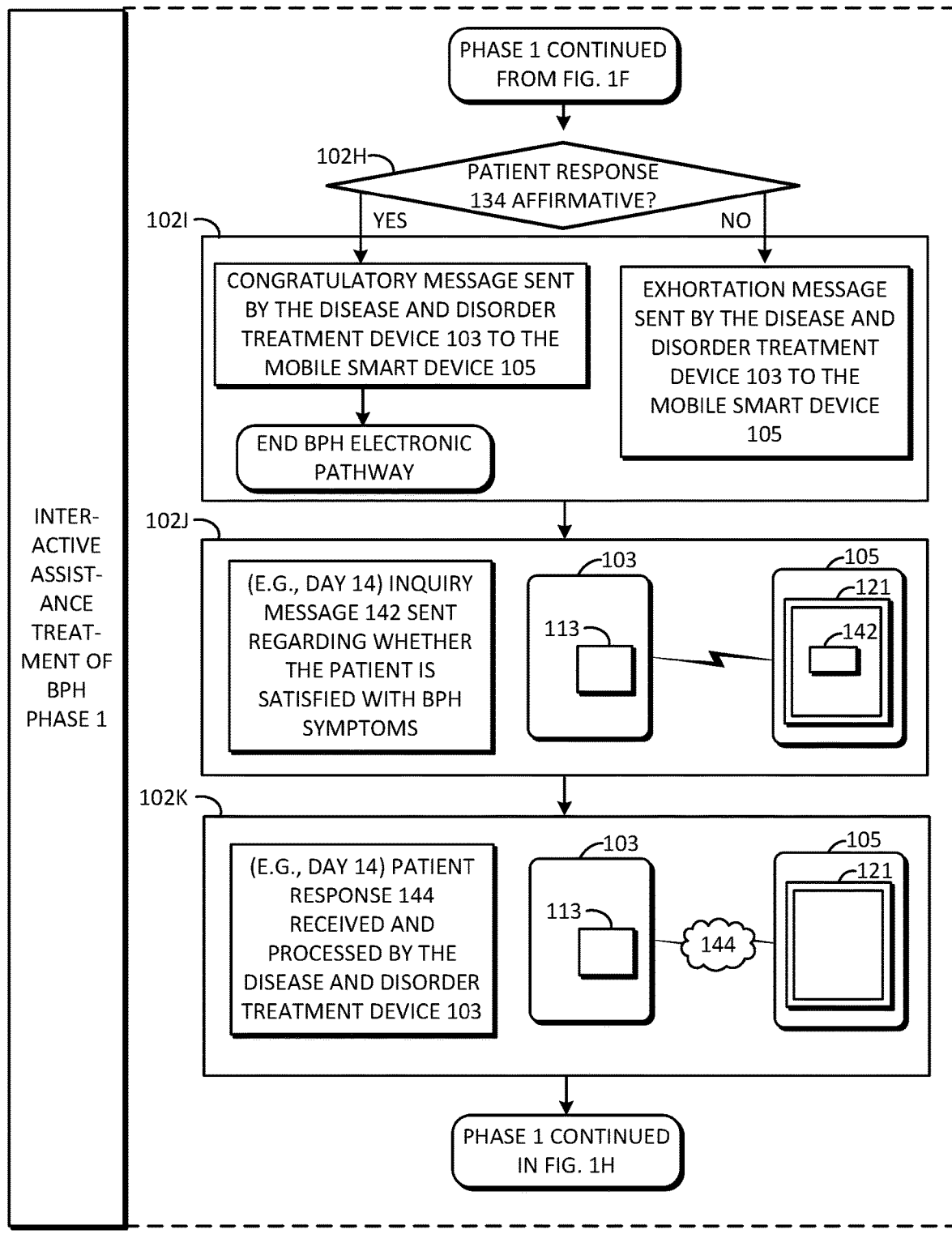
Figure 1H:
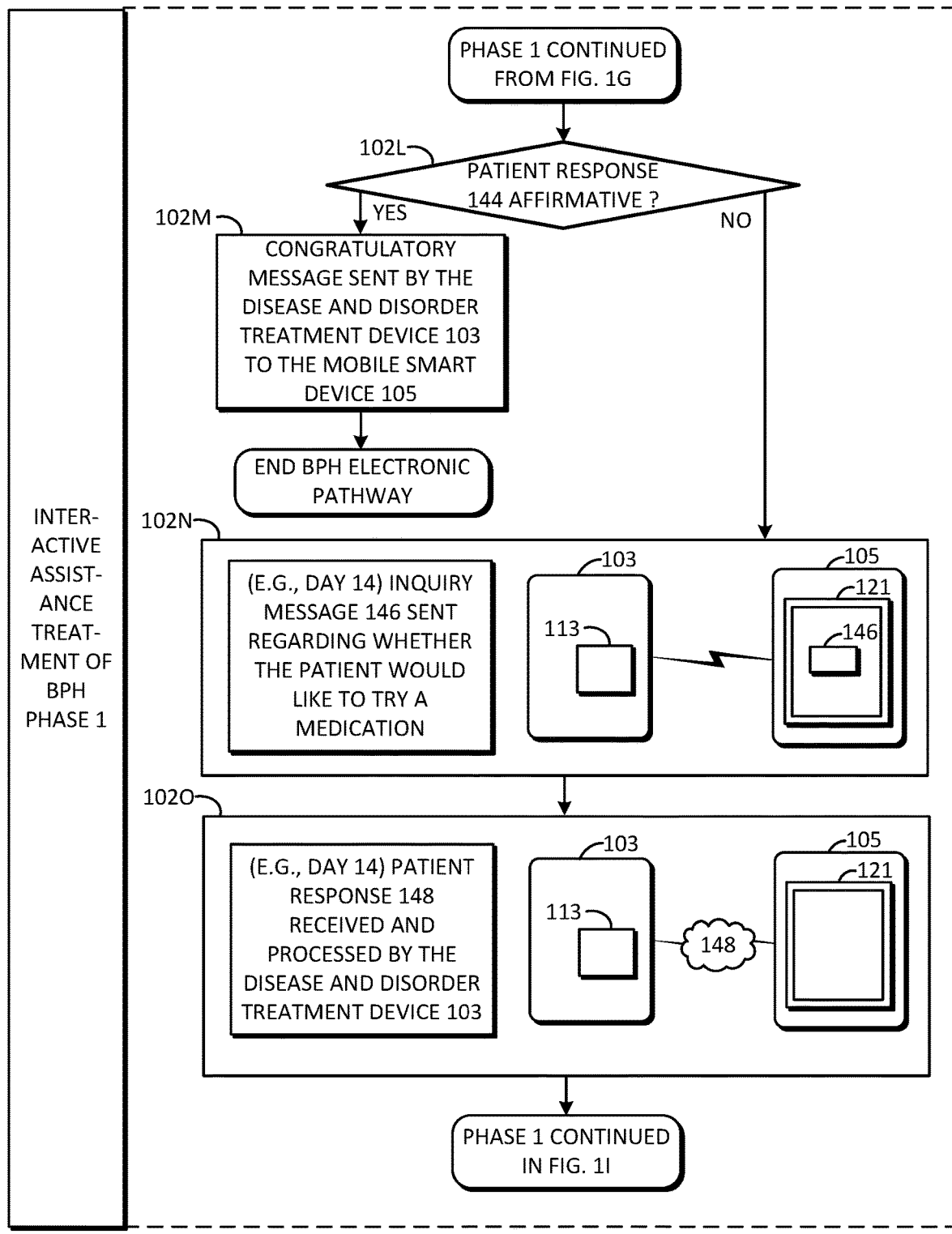
Figure 1I:
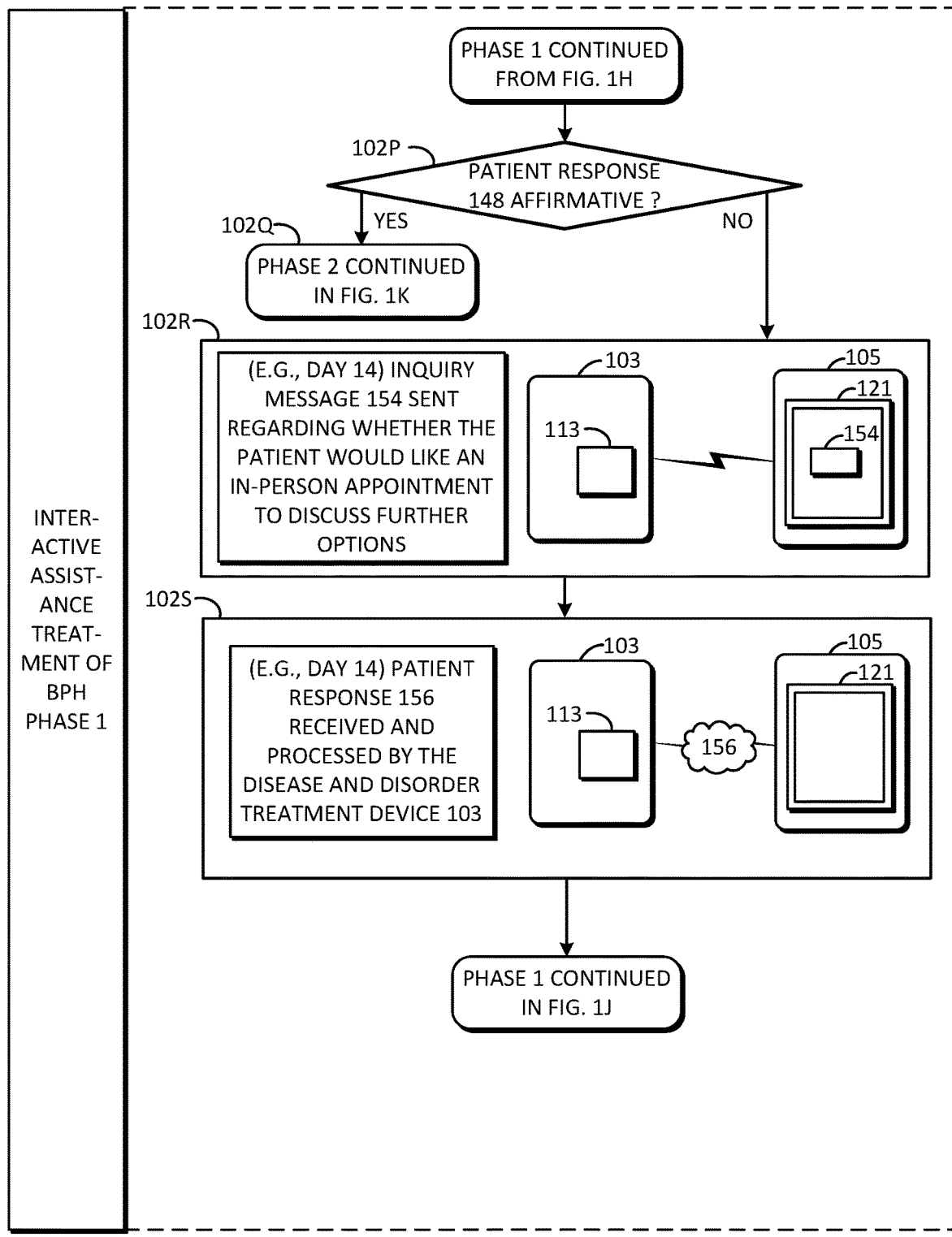
Figure 1J:
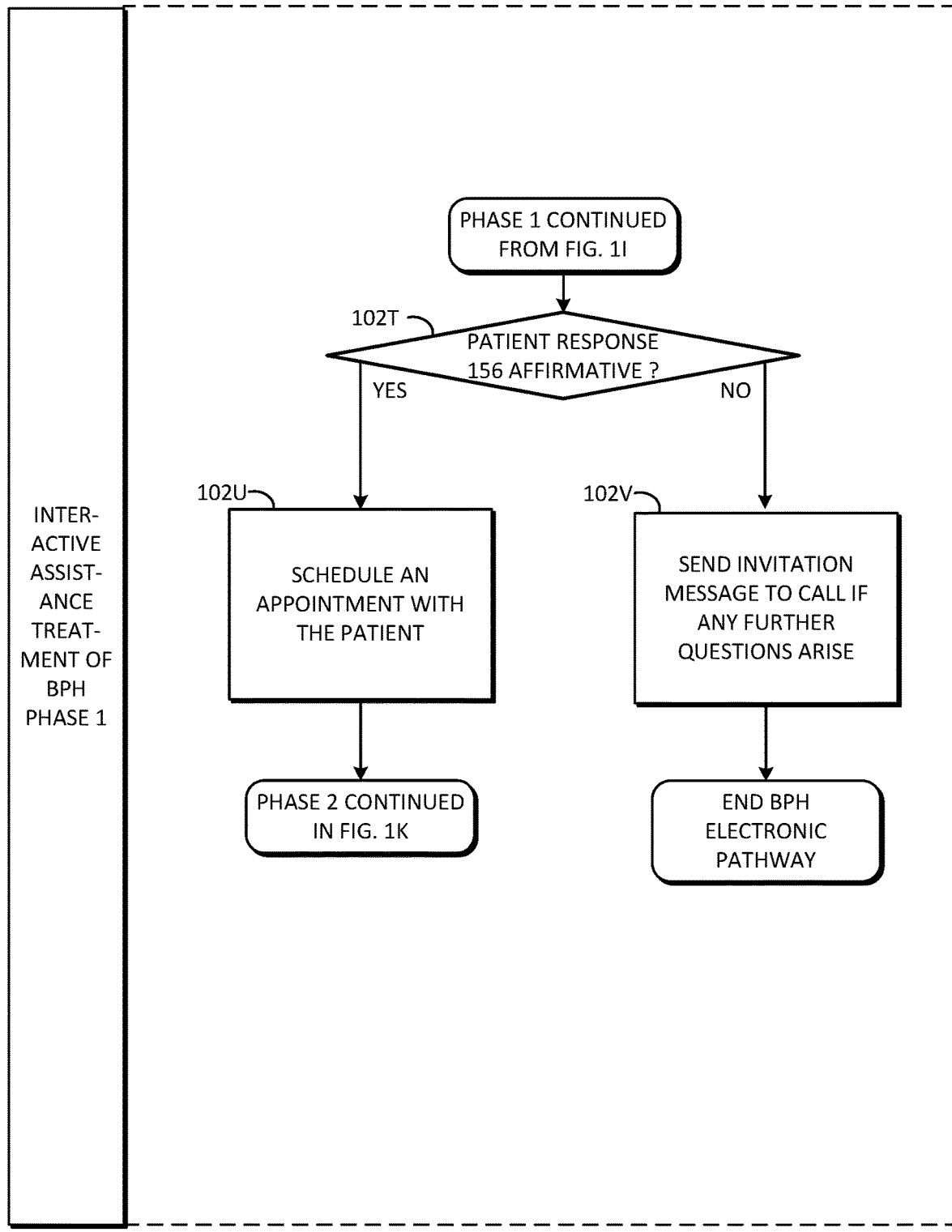

The steps shown at 102A of FIG. 1D are preparatory for the interactive assistance treatment that follows. For example, the BPH electronic pathway starts with an office visit. History and physical can be performed and basic testing such as uroflow, post void residual, urinalysis, prostate specific antigen (PSA), and electrolytes may be considered. The patient can be counseled on a four-phase electronic pathway for treatment of BPH. When the patient leaves the office, the patient can sign up for the BPH electronic pathway via an email or text sent by the healthcare provider inviting the patient to initiate the four-phase treatment pathway. For example, at 102B, the treatment assistant logic section 113 of the disease and disorder treatment device 103 can send a BPH electronic pathway signup link 116 via email or text message to the smart mobile device 105. At 102C, the disease and disorder treatment device 103 can receive signup information 118 from the patient. Once logged on, a series of educational slides 122 about BPH can be presented to the patient at 102D. The educational slides 122 can be sent by the disease and disorder treatment device 103 to the smart mobile device 105. Alternatively or in addition, the treatment assistance mobile logic section 125 of the smart mobile device 125 can store cause the educational slides 122 to be displayed on the touch-sensitive screen 121. Online resources including the educational material can be made available to the patient.

At 102E, the treatment assistant logic section 113 of the disease and disorder treatment device 103 can automatically send a reminder message 124 regarding the importance of aerobic exercise, weight lifting, heart-healthy diet, and adequate sleep for improving BPH to the smart mobile device 105 for display on the touch sensitive display 121. Alternatively or in addition, the treatment assistance mobile logic section 125 of the smart mobile device 105 can cause the reminder message 124 to be displayed on the touch sensitive display 121. The message 124 can be sent a predefined number of days (e.g., day 2) measured from the initiation of phase 1 of the interactive assistance treatment of BPH (e.g., measured from the time of receiving the sign-up information).

It will be understood that for all of the electronic interactions with the patient described herein, either the disease and disorder treatment device 103 or the smart mobile device 105, or both, can initiate the interaction with the patient. In other words, messages can be sent from the disease and disorder treatment device 103 to the smart mobile device 105 to be displayed. Alternatively, information already stored on the smart mobile device 105 can cause messages to be displayed on the touch-sensitive screen 121 of the smart mobile device 105. Responses from the patient can be stored locally on the smart mobile device 105 in the patient response storage unit 129.

Alternatively or in addition, responses from the patient can be transmitted, by the secure transceiver 119 of the smart mobile device 105 to the transceiver 109 of the disease and disorder treatment device 103 for storage in the patient response storage 117 of the disease and disorder treatment device 103. The disease and disorder treatment device 103 can store and aggregate patient responses from a plurality of patients, and can communicate with a plurality of smart mobile devices 105. While either the remote treatment assistance logic section 113 of the disease and disorder treatment device 103 or the local treatment assistance mobile logic section 125 of the smart mobile device 105, or both, can initiate and carry on the interactive communication with the patient, for the most part the description contained herein will assume that most interactions are initiated by the disease and disorder treatment device 103, carried out by the smart mobile device 105, and then responses transmitted back to the disease and disorder treatment device 103. For example, the main part of the description herein will assume that the patient query logic section 139, the patient instruction logic section 141, the patient response processing logic section 143, and the patient response storage interface logic section 145 of the treatment assistance logic section 113 of the disease and disorder treatment device 103 will initiate, process, and store some if not all of the interactive communications with the patient.

In alternative embodiments, some or all of the interactive communications described herein occur only as between the smart mobile device 103 and the patient, and are performed by the patient query logic section 139, the patient instruction logic section 141, the patient response processing logic section 143, and the patient response storage interface logic section 145 of the treatment assistance logic section 125 of the smart mobile device 105. It will be understood that any suitable combination of these components from either the disease and disorder treatment device 103 or the smart mobile device 105, or both, may be used in the interactive communications with the patient.

At 102F, the treatment assistant logic section 113 of the disease and disorder treatment device 103 can automatically send an inquiry message 132 regarding whether the patient has started an exercise program to the smart mobile device 105 for display on the touch sensitive display 121. At 102G, the disease and disorder treatment device 103 can automatically receive and process a response 134 of the patient from the smart mobile device 105. The message 132 and/or the response 134 can be sent a predefined number of days (e.g., day 7) from the initiation of phase 1 of the interactive assistance treatment of BPH.

At 102H, the patient response processing logic section 143 can automatically determine whether or not the patient response 134 is affirmative. If YES, then at 102I, the treatment assistant logic section 113 of the disease and disorder treatment device 103 can automatically send a congratulatory message to the smart mobile device 105 for display on the touch sensitive display 121. The message can include, for example, "Great keep up the good work." Otherwise, if NO, the treatment assistant logic section 113 of the disease and disorder treatment device 103 can automatically send an exhortation message to the smart mobile device 105 for display on the touch sensitive display 121. The message can include, for example, the words "Getting starting is the hardest part. There is no better time than now!"

At 102J, the treatment assistant logic section 113 of the disease and disorder treatment device 103 can automatically send an inquiry message 142 regarding whether the patient is satisfied with the BPH symptoms (i.e., whether the BPH symptoms have satisfactorily subsided) to the smart mobile device 105 for display on the touch sensitive display 121. At 102K, the treatment assistant logic section 113 of the disease and disorder treatment device 103 can automatically receive and process a response 144 of the patient from the smart mobile device 105. The message 142 and/or the response 144 can be sent a predefined number of days (e.g., day 14) from the initiation of phase 1 of the interactive assistance treatment of ED. At 102L, the patient response processing logic section 143 can automatically determine whether or not the patient response 144 is affirmative. If YES, then at 102M, the treatment assistant logic section 113 of the disease and disorder treatment device 103 can automatically send a congratulatory message to the smart mobile device 105 for display on the touch sensitive display 121. Each time after sending a congratulatory message, the treatment assistant logic section 113 of the disease and disorder treatment device 103 can automatically check back with the patient every three months (or other suitable period) to inquire about whether the patient is still satisfied. Otherwise, if NO, the treatment assistant logic section 113 of the disease and disorder treatment device 103 can automatically send an inquiry message 146 at 102N regarding whether the patient would like to try a medication to the smart mobile device 105 for display on the touch sensitive display 121. The treatment assistant logic section 113 of the disease and disorder treatment device 103 can automatically receive and process a response 148 at 102D of the user patient from the smart mobile device 105. The inquiry message 146 and/or the response 148 can be sent a predefined number of days (e.g., day 14) from the initiation of phase 1 of the interactive assistance treatment of BPH.

Figure 1K:
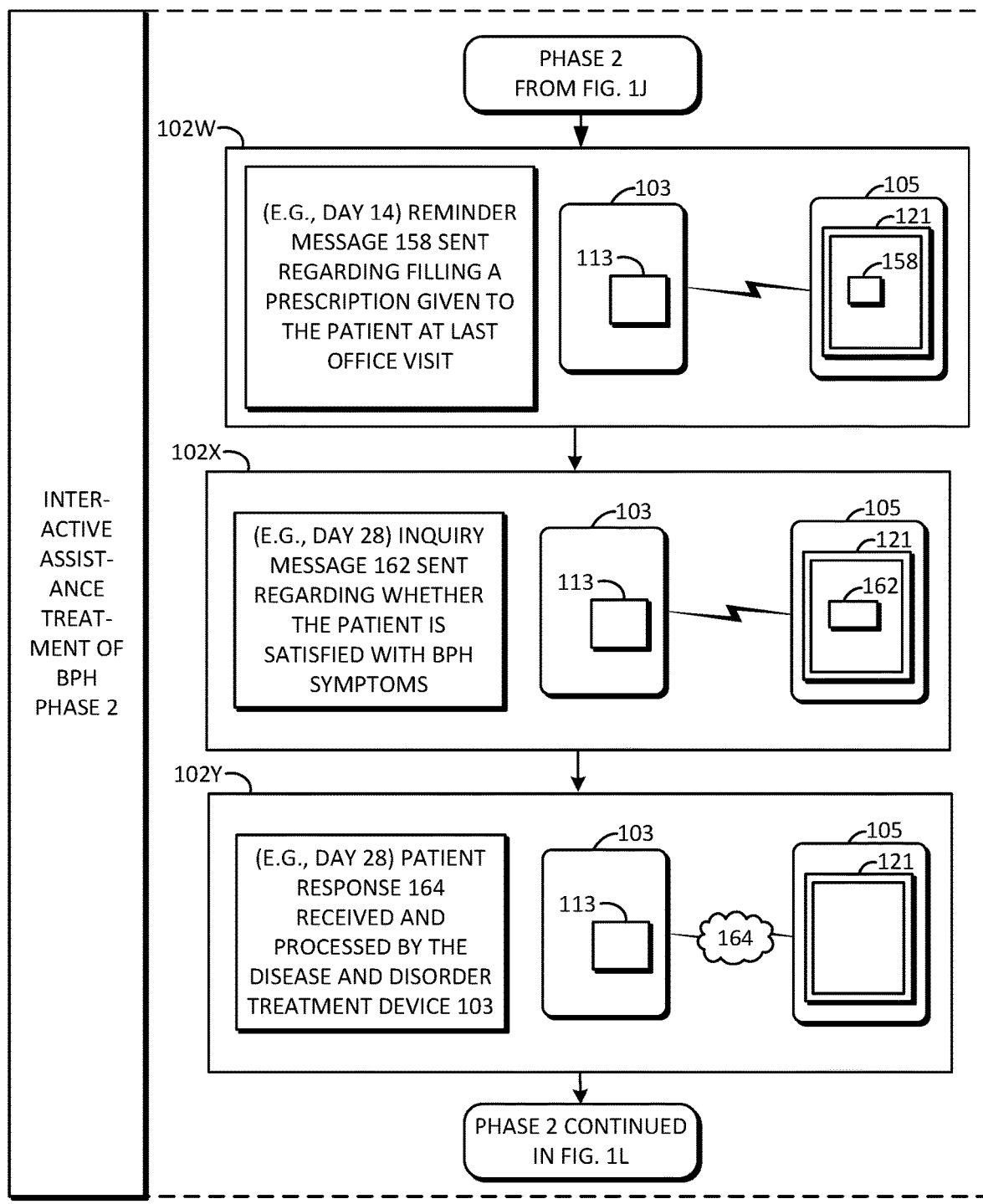
FIGS. 1K through 1N illustrate a block and flow diagram showing a second interactive treatment assistance phase related to BPH in accordance with various embodiments of the present inventive concept.
Figure 1L:
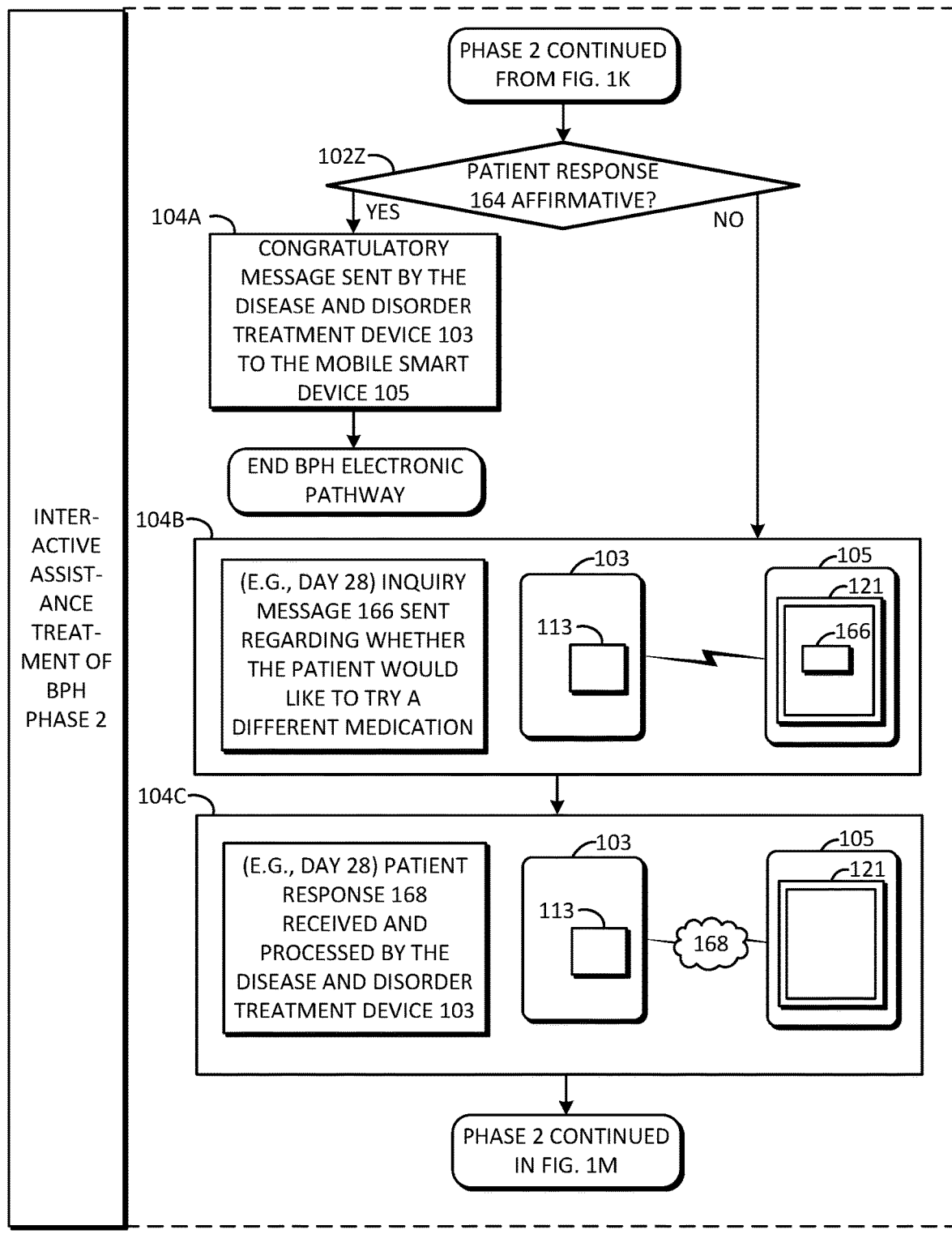
Figure 1M:
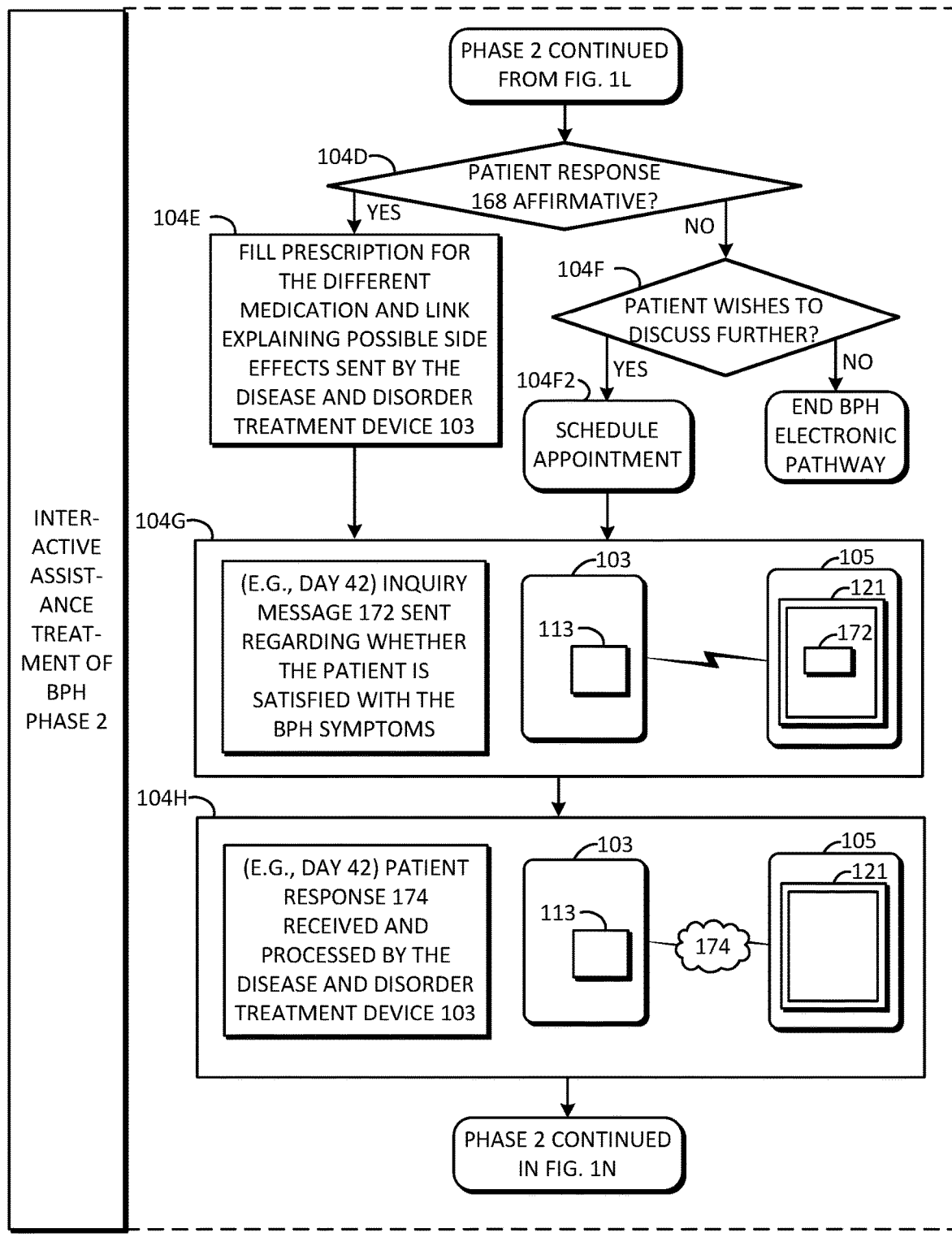
Figure 1N:
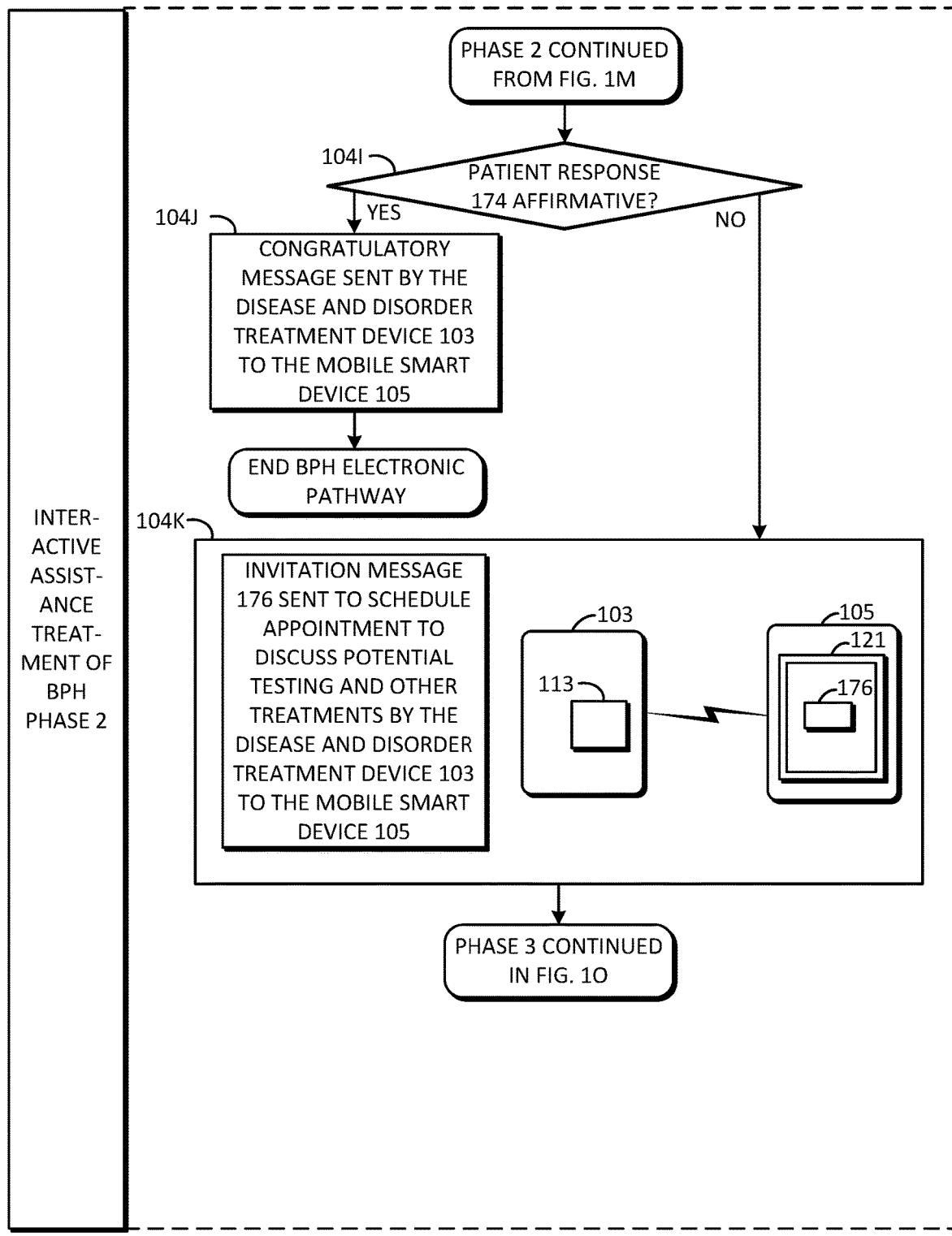

At 102P, the patient response processing logic section 143 can automatically determine whether or not the patient response 148 is affirmative. If YES, then at 102Q, the BPH electronic pathway can continue to phase 2 as illustrated in FIG. 1K. Otherwise, if NO, the treatment assistant logic section 113 of the disease and disorder treatment device 103 can automatically send an inquiry message 154 regarding whether the patient would like an in-person appointment to discuss further options to the smart mobile device 105 for display on the touch sensitive display 121. At 102S, the treatment assistant logic section 113 of the disease and disorder treatment device 103 can automatically receive and process a response 156 of the user patient from the smart mobile device 105. The inquiry message 154 and/or the response 156 can be sent a predefined number of days (e.g., day 14) from the initiation of phase 1 of the interactive assistance treatment of BPH.

At 102T, the patient response processing logic section 143 can automatically determine whether or not the patient response 156 is affirmative. If YES, then at 102U, then the disease and disorder treatment device 103 can facilitate the scheduling of an appointment between the health care provider and the patient, after which the BPH electronic pathway can continue with phase 2 in FIG. 1K. Otherwise, if NO, then at 102V the treatment assistant logic section 113 of the disease and disorder treatment device 103 can automatically send an invitation message to the patient to call if any further questions arise, after which the BPH electronic pathway can end.

FIGS. 1K through 1N illustrate a block and flow diagram showing a second interactive treatment assistance phase related to BPH in accordance with various embodiments of the present inventive concept. At 102W, the treatment assistant logic section 113 of the disease and disorder treatment device 103 can automatically send a reminder message 158 regarding filling a prescription that was given to the patient at the last office visit to the smart mobile device 105 for display on the touch sensitive display 121. At 102X, the treatment assistant logic section 113 of the disease and disorder treatment device 103 can automatically send an inquiry message 162 regarding whether the patient is satisfied with the BPH symptoms (i.e., whether the BPH symptoms have satisfactorily subsided) to the smart mobile device 105 for display on the touch sensitive display 121. At 102Y, the treatment assistant logic section 113 of the disease and disorder treatment device 103 can automatically receive and process a response 164 of the user patient from the smart mobile device 105. The inquiry message 162 and/or the response 164 can be sent a predefined number of days (e.g., day 28) from the initiation of phase 1 of the interactive assistance treatment of BPH.

At 102Z, the patient response processing logic section 143 can automatically determine whether or not the patient response 164 is affirmative. If YES, then at 104A, the treatment assistant logic section 113 of the disease and disorder treatment device 103 can automatically send a congratulatory message to the smart mobile device 105 for display on the touch sensitive display 121. Otherwise, if NO, then the phase 2 of the BPH electronic pathway can continue to 104B, where the treatment assistant logic section 113 of the disease and disorder treatment device 103 can automatically send an inquiry message 166 regarding whether the patient would like to try a different medication to the smart mobile device 105 for display on the touch sensitive display 121. At 104C, the treatment assistant logic section 113 of the disease and disorder treatment device 103 can automatically receive and process a response 168 of the user patient from the smart mobile device 105. The inquiry message 166 and/or the response 168 can be sent a predefined number of days (e.g., day 28) from the initiation of phase 1 of the interactive assistance treatment of BPH.

At 104D, the patient response processing logic section 143 can automatically determine whether or not the patient response 168 is affirmative. If YES, then at 104E, the treatment assistant logic section 113 of the disease and disorder treatment device 103 can facilitate the filling of the prescription for the different medication, and automatically send a link explaining possible side effects to the smart mobile device 105 for display on the touch sensitive display 121. Otherwise, if NO, the treatment assistant logic section 113 of the disease and disorder treatment device 103 can automatically send an inquiry message at 104F whether the patient wishes to discuss further options. If YES, then at 104F2, the treatment assistant logic section 113 of the disease and disorder treatment device 103 can facilitate the scheduling of an appointment with the health care provider. Otherwise, if NO, then the BPH electronic pathway can end.

At 104G, the treatment assistant logic section 113 of the disease and disorder treatment device 103 can automatically send an inquiry message 172 regarding whether the patient is satisfied with the BPH symptoms (i.e., whether the BPH symptoms have satisfactorily subsided) to the smart mobile device 105 for display on the touch sensitive display 121. At 104H, the treatment assistant logic section 113 of the disease and disorder treatment device 103 can automatically receive and process a response 174 of the user patient from the smart mobile device 105. The inquiry message 172 and/or the response 174 can be sent a predefined number of days (e.g., day 42) from the initiation of phase 1 of the interactive assistance treatment of BPH.

At 104I, the patient response processing logic section 143 can automatically determine whether or not the patient response 174 is affirmative. If YES, then at 104J, the treatment assistant logic section 113 of the disease and disorder treatment device 103 can send a congratulatory message to the smart mobile device 105 for display on the touch sensitive display 121. Otherwise, if NO, the treatment assistant logic section 113 of the disease and disorder treatment device 103 can automatically send an invitation message at 104K to schedule an appointment to discuss potential testing and other treatments to the smart mobile device 105 for display on the touch sensitive display 121. Alternatively or in addition, the treatment assistant logic section 113 of the disease and disorder treatment device 103 can facilitate the making of the appointment with the health care provider. The BPH electronic pathway can then proceed to phase 3 as illustrated in FIG. 1O.

Figure 1O:
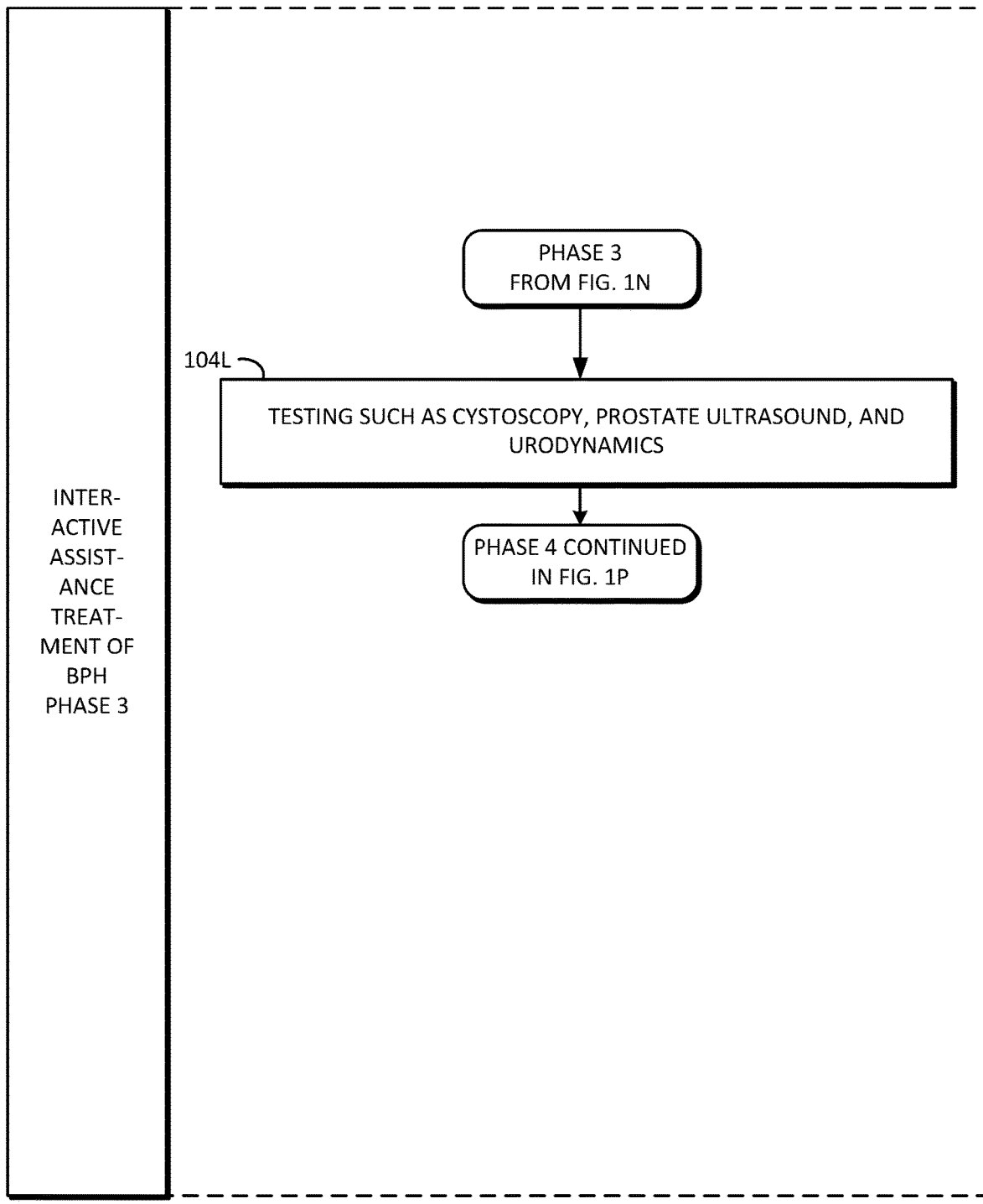
FIG. 1O illustrates a block and flow diagram showing a third interactive treatment assistance phase related to BPH in accordance with various embodiments of the present inventive concept.
Figure 1P:
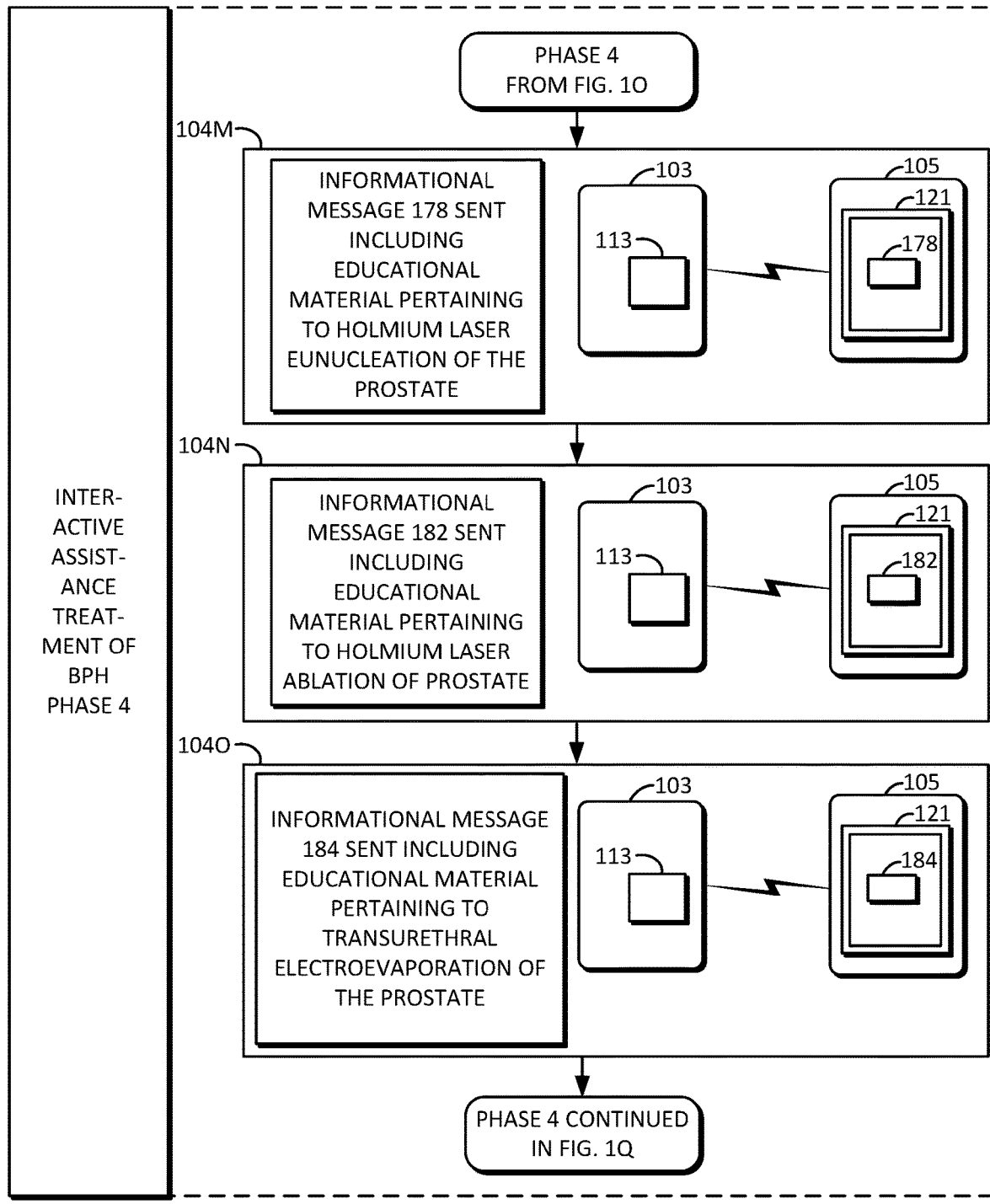
FIGS. 1P through 1S illustrate a block and flow diagram showing a fourth interactive treatment assistance phase related to BPH in accordance with various embodiments of the present inventive concept.
Figure 1Q:
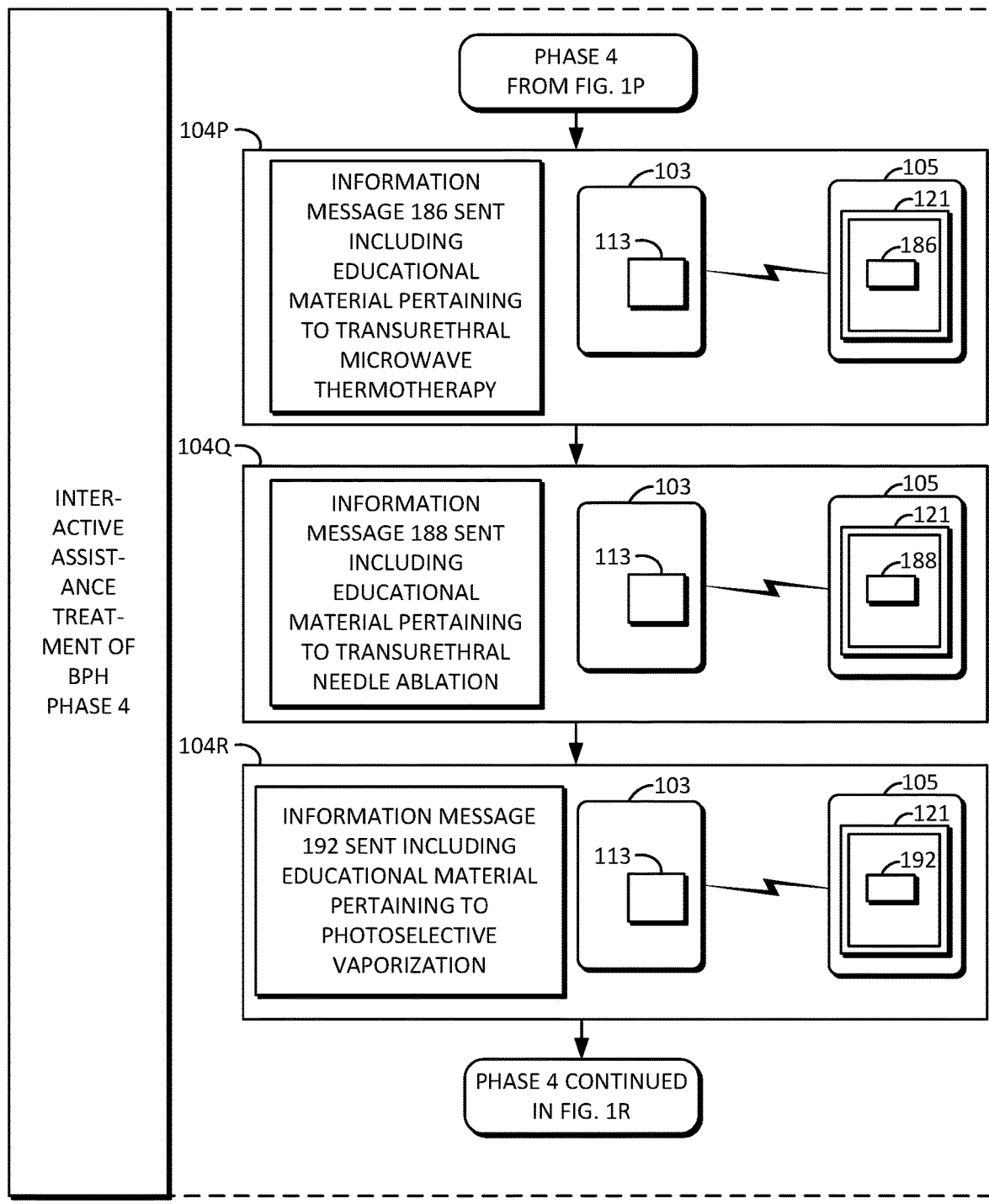
Figure 1R:
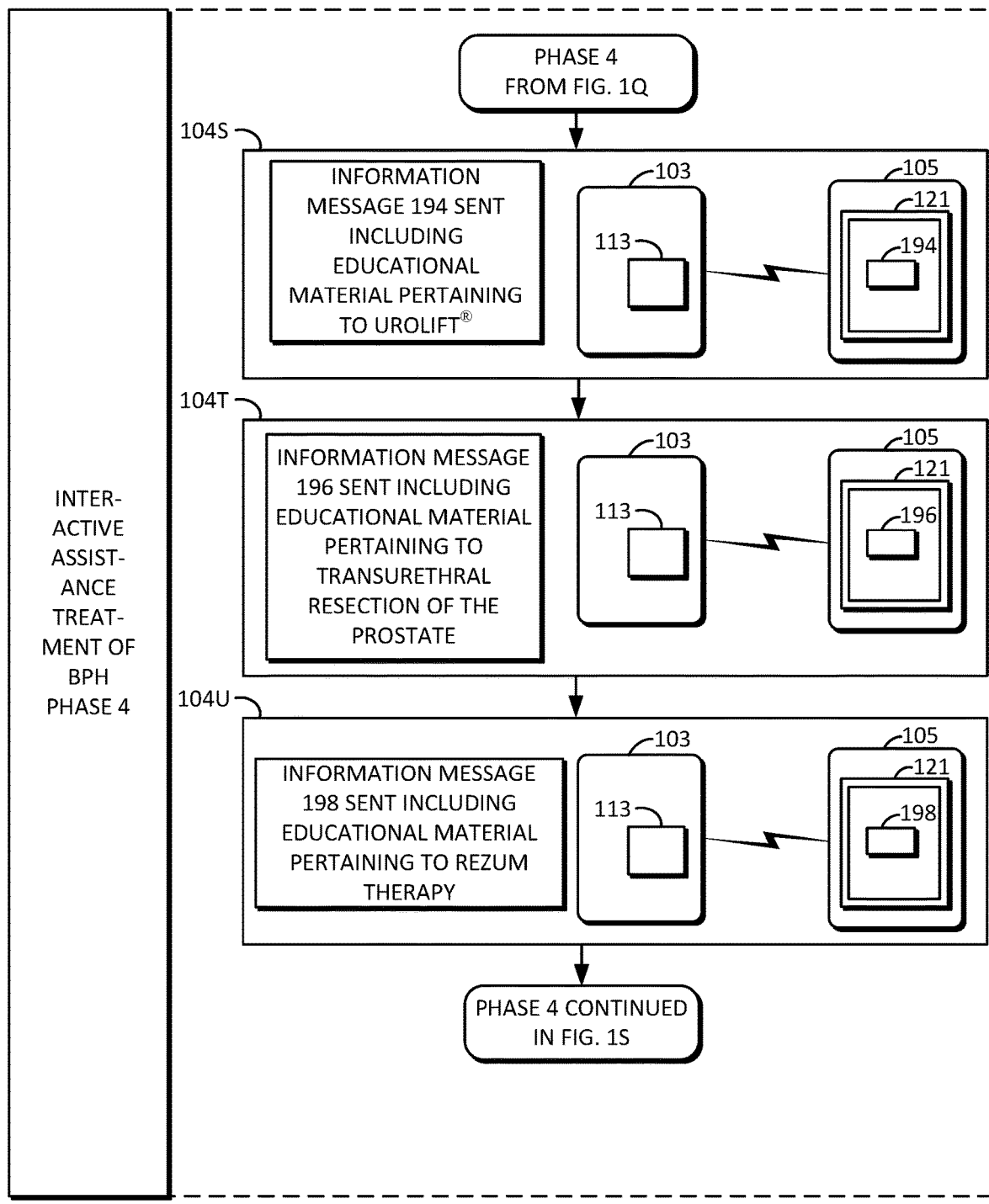
Figure 1S:
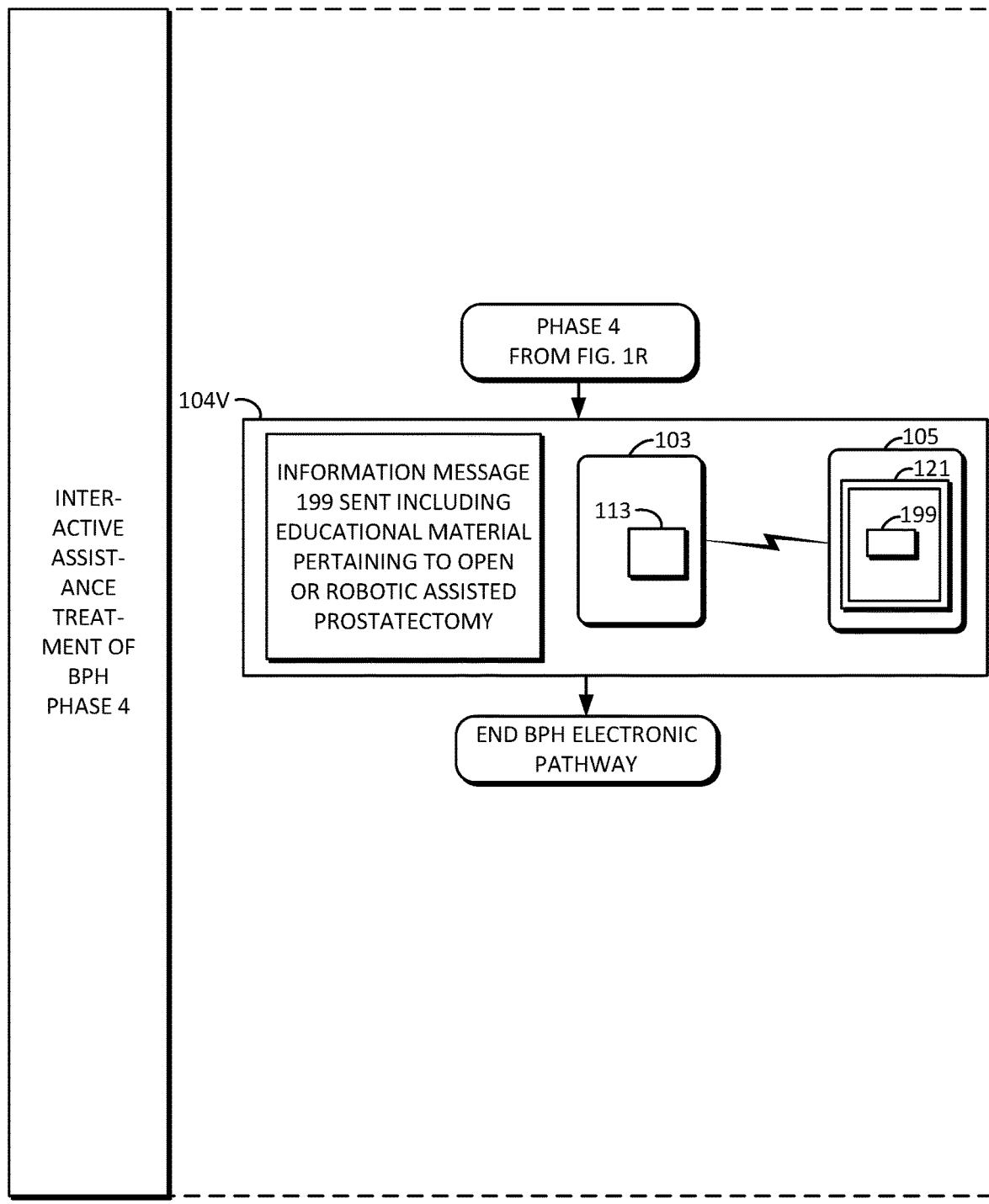

FIG. 1O illustrates a block and flow diagram showing a third interactive treatment assistance phase related to BPH in accordance with various embodiments of the present inventive concept. At 104L, the health care provider can perform testing such as cystoscopy, prostate ultrasound, and/or urodynamics. The BPH electronic pathway can then proceed to phase 4 as illustrated in FIG. 1P for advanced treatments such as procedures and surgeries.

FIGS. 1P through 1S illustrate a block and flow diagram showing a fourth interactive treatment assistance phase related to BPH in accordance with various embodiments of the present inventive concept. At 104M, the treatment assistant logic section 113 of the disease and disorder treatment device 103 can automatically send an informational message 178 including educational material pertaining to holmium laser enunucleation of the prostate to the smart mobile device 105 for display on the touch sensitive display 121. At 104N, the treatment assistant logic section 113 of the disease and disorder treatment device 103 can automatically send an informational message 182 including educational material pertaining to holmium laser ablation of the prostate to the smart mobile device 105 for display on the touch sensitive display 121. At 104O, the treatment assistant logic section 113 of the disease and disorder treatment device 103 can automatically send an informational message 184 including educational material pertaining to holmium transurethral electroevaporation of the prostate to the smart mobile device 105 for display on the touch sensitive display 121. At 104P, the treatment assistant logic section 113 of the disease and disorder treatment device 103 can automatically send an informational message 186 including educational material pertaining to transurethral microwave thermotherapy of the prostate to the smart mobile device 105 for display on the touch sensitive display 121. At 104Q, the treatment assistant logic section 113 of the disease and disorder treatment device 103 can automatically send an informational message 188 including educational material pertaining to transurethral needle ablation of the prostate to the smart mobile device 105 for display on the touch sensitive display 121. At 104R, the treatment assistant logic section 113 of the disease and disorder treatment device 103 can automatically send an informational message 192 including educational material pertaining to photoselective vaporization of the prostate to the smart mobile device 105 for display on the touch sensitive display 121.

At 104S, the treatment assistant logic section 113 of the disease and disorder treatment device 103 can automatically send an informational message 194 including educational material pertaining to urolift to the smart mobile device 105 for display on the touch sensitive display 121. At 104T, the treatment assistant logic section 113 of the disease and disorder treatment device 103 can automatically send an informational message 196 including educational material pertaining to transurethral resection of the prostate to the smart mobile device 105 for display on the touch sensitive display 121. At 104U, the treatment assistant logic section 113 of the disease and disorder treatment device 103 can automatically send an informational message 198 including educational material pertaining to rezum to the smart mobile device 105 for display on the touch sensitive display 121. At 104V, the treatment assistant logic section 113 of the disease and disorder treatment device 103 can automatically send an informational message 199 including educational material pertaining to open or robotic assisted prostatectomy of the prostate to the smart mobile device 105 for display on the touch sensitive display 121.

Figure 2:
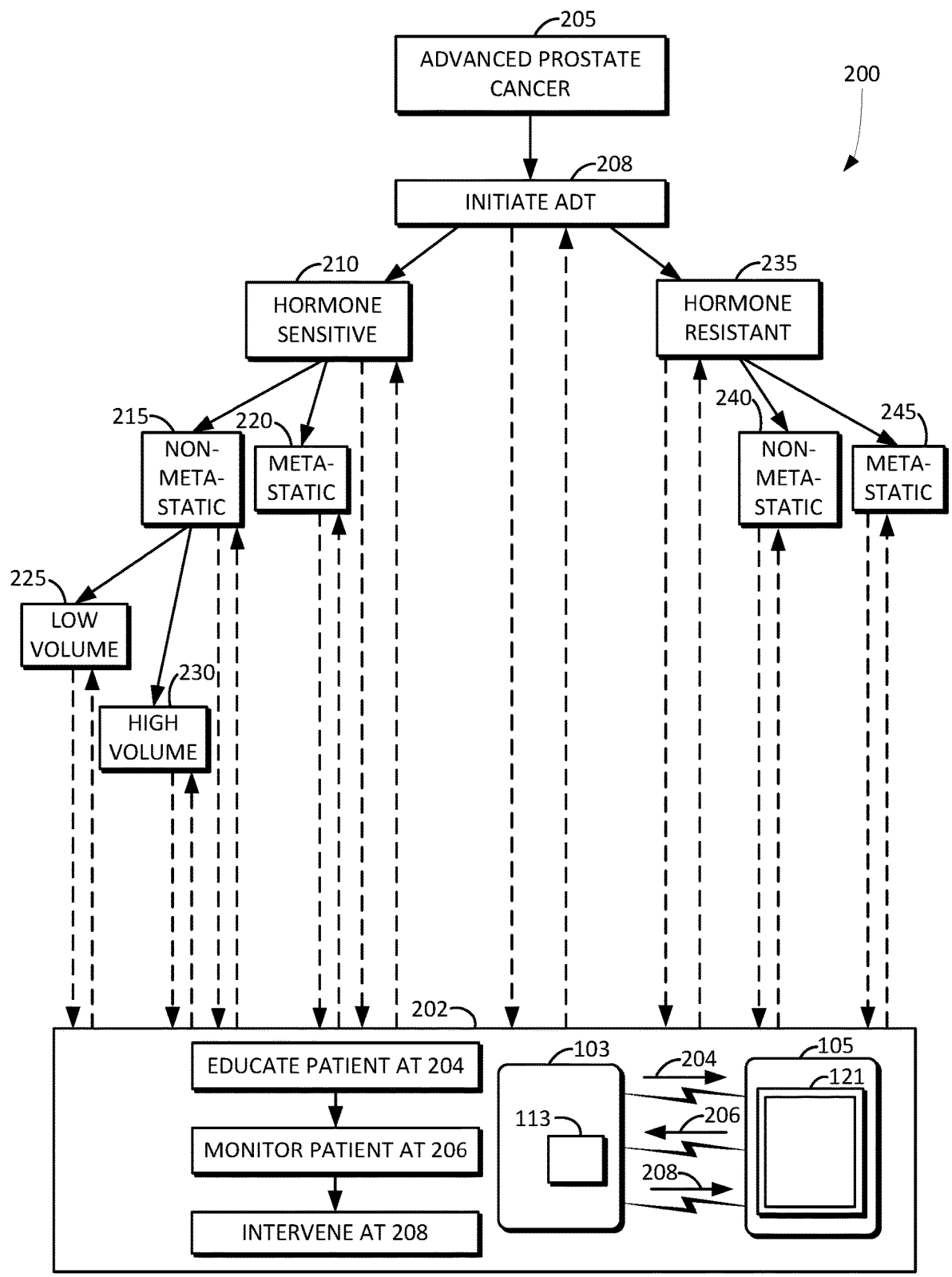
FIG. 2 illustrates a block and flow diagram showing an interactive treatment assistance technique related to advanced prostate cancer in accordance with various embodiments of the present inventive concept.

FIG. 2 illustrates a block and flow diagram 200 showing an interactive treatment assistance technique related to advanced prostate cancer in accordance with various embodiments of the present inventive concept. Reference is now made to FIGS. 1A through 1C, and FIG. 2.

The options for care, testing, and educational information for both health care practitioners and patients are very complex. The disease and disorder treatment device 103 (of FIG. 1A) and/or the mobile smart device 105 include treatment assistant logic (e.g., 113 and 125 of FIG. 1A) can help the patient and healthcare provider by directing a clear treatment pathway for advanced prostate cancer treatment. These techniques provide the patient and the health care provider with education and an interactive environment in which the patient can be automatically monitored, and intervention or action taken with regard to a specific phase of the disorder or disease. This includes side effects of the various medications, importance of bone health, and available clinical trials. In addition, user patient alerts can be generated regarding daily supplements, dietary adjustments, and weight-bearing exercise. The healthcare provider can receive alerts regarding diagnostic labs and imaging, appropriate treatment options, and/or clinical trials available. The treatment assistant logic (e.g., 113 and 125 of FIG. 1A) is designed for a navigator to oversee the electronic pathway for an entire group or several groups of patients. The treatment assistant logic (e.g., 113 and 125 of FIG. 1A) can contact patients directly via an application that runs on the smart mobile device 103, email, text, or any suitable combination thereof.

As shown in FIG. 2, when a patient is diagnosed with advanced prostate cancer at 205, then androgen deprivation therapy (ADT) can be initiated at 208. At 202, the treatment assistant logic section 113 of the disease and disorder treatment device 103 can automatically educate the patient at 204 by sending educational information to the smart mobile device 105 for display on the touch-sensitive screen 121. At 206, the treatment assistant logic section 113 of the disease and disorder treatment device 103 can automatically monitor the ADT by receiving feedback and other responses of the patient from the smart mobile device 105. At 208, the treatment assistant logic section 113 of the disease and disorder treatment device 103 can automatically intervene when the patient experiences symptoms or other adverse effects during the ADT treatment.

There are various kinds of characteristics associated with advanced prostate cancer. One characteristic is associated with a hormone sensitive form of the disease as shown at 210. The hormone sensitive form of the disease may be non-metastatic 215 or metastatic 220. If categorized as non-metastatic 215, the disease may be low volume 225 or high volume 230. Depending on specific characteristics associated with the form of prostate cancer that a particular patient might have, the treatment assistant logic section 113 of the disease and disorder treatment device 103 can automatically tailor the electronic pathway for educating, monitoring, and intervening on behalf of the patient.

For example, the treatment assistant logic section 113 of the disease and disorder treatment device 103 can automatically provide educational material at 204 to the patient that is tailored to the specific characteristics of the particular form of prostate cancer that the patient has. By way of another example, the treatment assistant logic section 113 of the disease and disorder treatment device 103 can automatically monitor the patient at 206 for symptoms and challenges associated with the specific characteristics of the particular form of prostate cancer that the patient has. By way of yet another example, the treatment assistant logic section 113 of the disease and disorder treatment device 103 can automatically intervene at 208 and make alterations to treatment or suggestions to take action for display on the smart mobile device 105, depending on the results of the monitoring.

Another characteristic of advanced prostate cancer may be a hormone sensitive form of the disease as shown at 235. The hormone sensitive form of the disease may be non-metastatic 240 or metastatic 245. As explained above, depending on specific characteristics associated with the form of prostate cancer that a particular patient might have, the treatment assistant logic section 113 of the disease and disorder treatment device 103 can automatically tailor the electronic pathway for educating, monitoring, and intervening on behalf of the patient.

Figure 3:
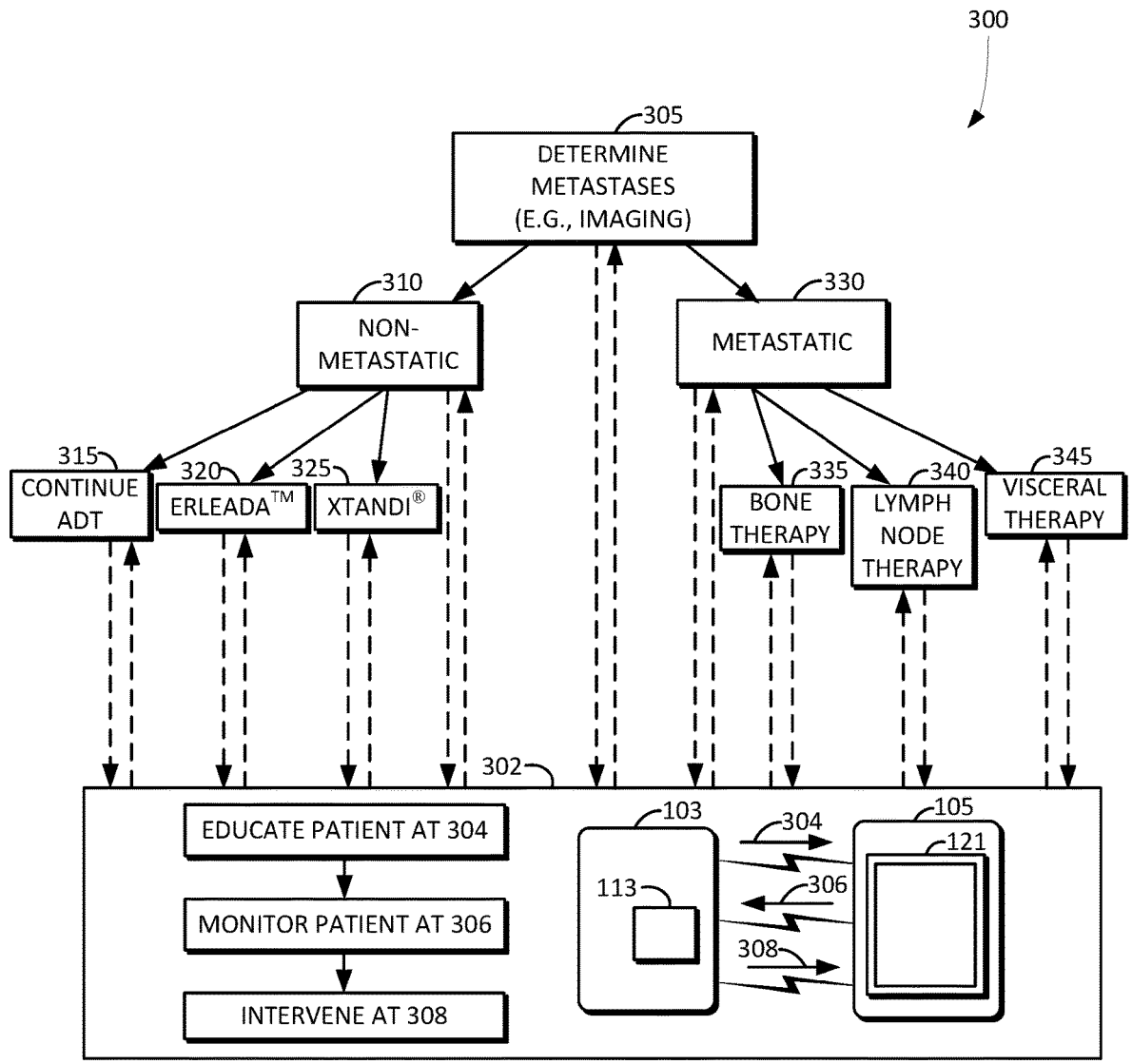
FIG. 3 illustrates a block and flow diagram showing an interactive treatment assistance technique related to metastases of advanced prostate cancer in accordance with various embodiments of the present inventive concept.

FIG. 3 illustrates a block and flow diagram 300 showing an interactive treatment assistance technique related to metastases of advanced prostate cancer in accordance with various embodiments of the present inventive concept. At 305, a health care provider may determine the extent (if any) of metastases based, for example, on one or more imaging tests. Depending on specific characteristics associated with the form of metastases that a particular patient might be experiencing, the treatment assistant logic section 113 of the disease and disorder treatment device 103 can automatically tailor the electronic pathway for educating, monitoring, and intervening on behalf of the patient. In the case of non-metastatic prostate cancer as shown at 310, the treatment assistant logic section 113 of the disease and disorder treatment device 103 can automatically assist in the treatment by encouraging the patient to continue with ADT as shown at 315, and/or to facilitate the implementation of other specific treatments such as Erleada™ 320 or Xtandi® 325. In the case of metastatic prostate cancer as shown at 330, the treatment assistant logic section 113 of the disease and disorder treatment device 103 can automatically assist in the implementation of bone therapy 335, lymph nodes and/or soft tissue therapy 340, and/or visceral therapy 345, as further described below.

For example, at 302, the treatment assistant logic section 113 of the disease and disorder treatment device 103 can automatically educate the patient at 304 by sending educational information that is tailored to the specific characteristics of the metastases to the smart mobile device 105 for display on the touch-sensitive screen 121. At 306, the treatment assistant logic section 113 of the disease and disorder treatment device 103 can automatically monitor the metastases by receiving feedback and other responses of the patient from the smart mobile device 105. At 308, the treatment assistant logic section 113 of the disease and disorder treatment device 103 can automatically intervene when the patient experiences symptoms or other adverse effects during the treatment.

Figure 4:
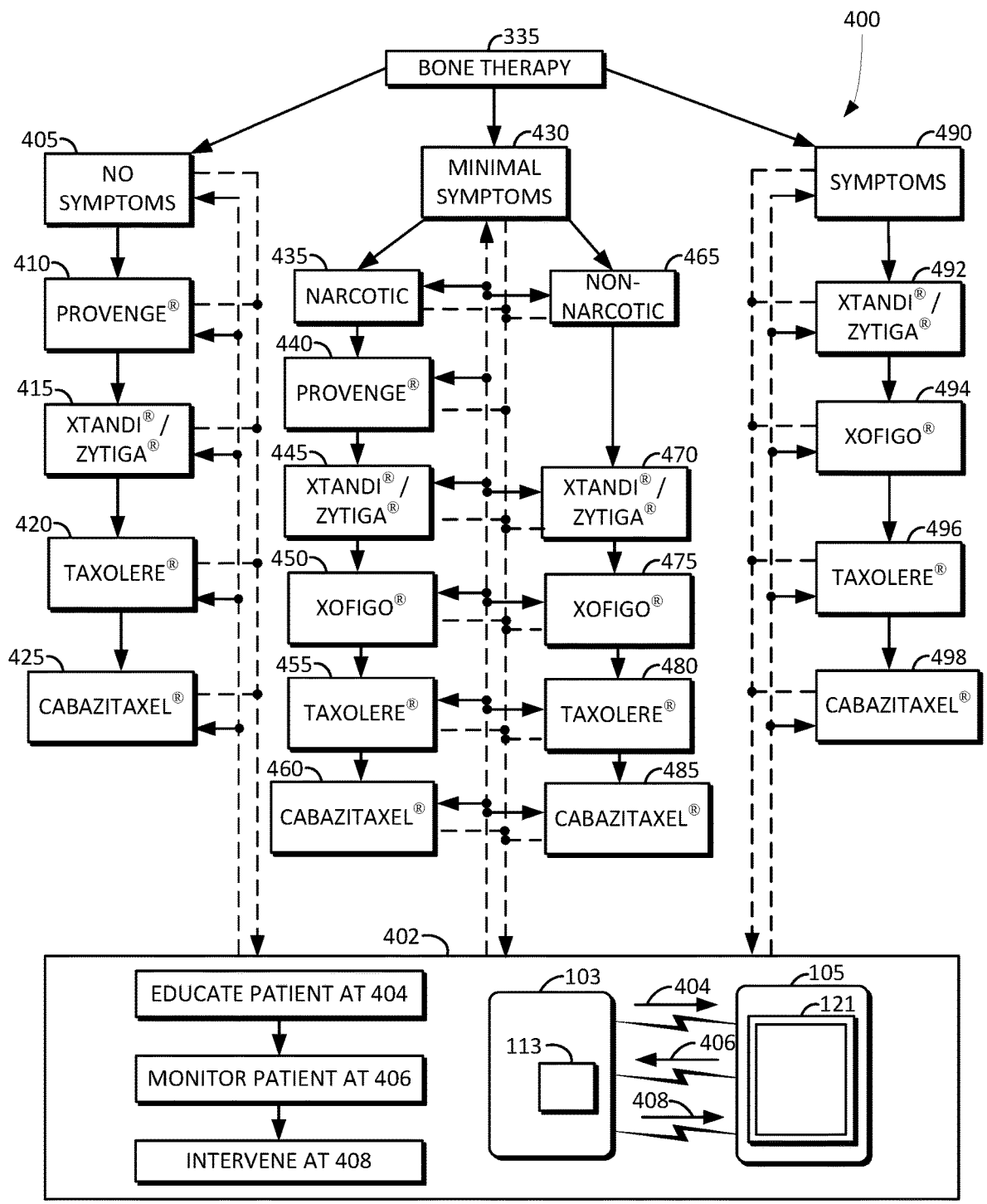
FIG. 4 illustrates a block and flow diagram showing an interactive treatment assistance technique related to bone therapy in accordance with various embodiments of the present inventive concept.

FIG. 4 illustrates a block and flow diagram 400 showing an interactive treatment assistance technique related to bone therapy in accordance with various embodiments of the present inventive concept. At 335, bone therapy begins. Depending on specific characteristics associated with the form of prostate cancer that the patient might be experiencing, the treatment assistant logic section 113 of the disease and disorder treatment device 103 can automatically tailor the electronic pathway for educating, monitoring, and intervening on behalf of the patient. The patient may be experiencing no symptoms 405, minimal symptoms 430, or some symptoms 490. In the case of no symptoms as shown at 405, the treatment assistant logic section 113 of the disease and disorder treatment device 103 can automatically assist in the treatment by facilitating the implementation and monitoring of specific treatments such as Provenge® 410, followed by Xtandi®/Zytiga® 415 if necessary, followed by Taxolere® 420 if necessary, followed by Cabazitaxel® 425 if necessary.

In the case of minimal symptoms as shown at 430, the treatment assistant logic section 113 of the disease and disorder treatment device 103 can automatically assist in the bone therapy 335 using one or more narcotics 435 and/or one or more non-narcotics 465. In the case of using one or more narcotics 435, the treatment assistant logic section 113 of the disease and disorder treatment device 103 can automatically assist in the treatment by facilitating the implementation and monitoring of specific treatments such as Provenge® 440, followed by Xtandi®/Zytiga® 445 if necessary, followed by Xofigo® 450 if necessary, followed by Taxolere® 455 if necessary, followed by Cabazitaxel® 460 if necessary. In the case of using one or more non-narcotics 465, the treatment assistant logic section 113 of the disease and disorder treatment device 103 can automatically assist in the treatment by facilitating the implementation and monitoring of specific treatments such as Xtandi®/Zytiga® 470, followed by Xofigo® 475 if necessary, followed by Taxolere® 480 if necessary, followed by Cabazitaxel® 485 if necessary.

In the case of some symptoms as shown at 490, the treatment assistant logic section 113 of the disease and disorder treatment device 103 can automatically assist in the treatment by facilitating the implementation and monitoring of specific treatments such as Xtandi®/Zytiga® 492, followed by Xofigo® 494 if necessary, followed by Taxolere® 496 if necessary, followed by Cabazitaxel® 498 if necessary.

For example, at 402, the treatment assistant logic section 113 of the disease and disorder treatment device 103 can automatically educate the patient at 404 by sending educational information that is tailored to the specific characteristics of the bone therapy 335 to the smart mobile device 105 for display on the touch-sensitive screen 121. At 406, the treatment assistant logic section 113 of the disease and disorder treatment device 103 can automatically monitor the bone therapy 335 by receiving feedback and other responses of the patient from the smart mobile device 105. At 408, the treatment assistant logic section 113 of the disease and disorder treatment device 103 can automatically intervene when the patient experiences symptoms or other adverse effects during the treatment. The treatment assistant logic section 113 can assist the patient at each step during the bone therapy 335, such as by educating, monitoring patient condition, facilitating new prescriptions, and intervening in the therapy when necessary to improve the chances that the patient survives.

Figure 5:
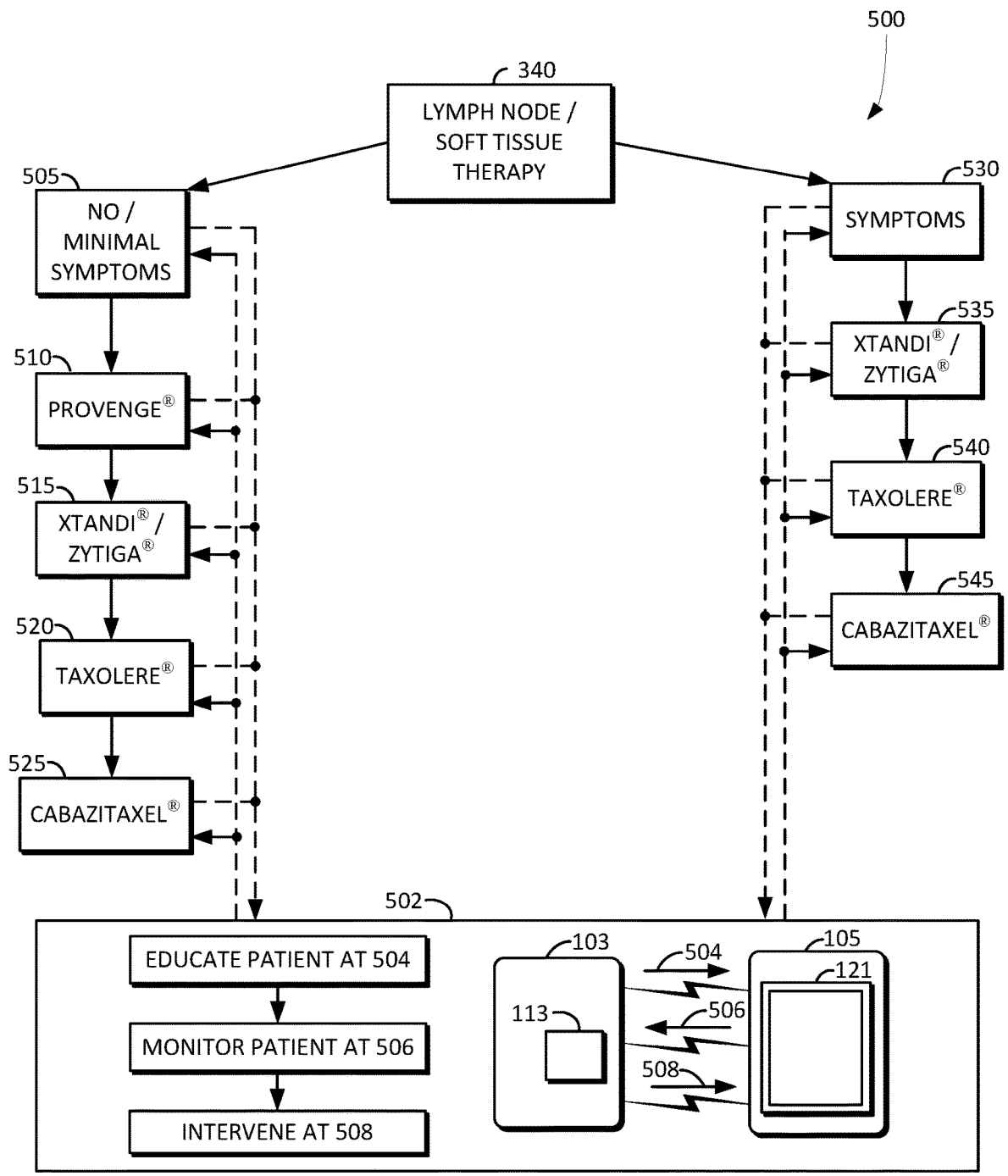
FIG. 5 illustrates a block and flow diagram showing an interactive treatment assistance technique related to lymph node/soft tissue therapy in accordance with various embodiments of the present inventive concept.

FIG. 5 illustrates a block and flow diagram 500 showing an interactive treatment assistance technique related to lymph node and/or soft tissue therapy in accordance with various embodiments of the present inventive concept. At 340, lymph node and/or soft tissue therapy begins. Depending on specific characteristics associated with the form of prostate cancer that the patient might be experiencing, the treatment assistant logic section 113 of the disease and disorder treatment device 103 can automatically tailor the electronic pathway for educating, monitoring, and intervening on behalf of the patient. The patient may be experiencing no or minimal symptoms 505, or some symptoms 530. In the case of no or minimal symptoms as shown at 505, the treatment assistant logic section 113 of the disease and disorder treatment device 103 can automatically assist in the treatment by facilitating the implementation and monitoring of specific treatments such as Provenge® 510, followed by Xtandi®/Zytiga® 515 if necessary, followed by Taxolere® 520 if necessary, followed by Cabazitaxel® 525 if necessary.

In the case of some symptoms as shown at 530, the treatment assistant logic section 113 of the disease and disorder treatment device 103 can automatically assist in the treatment by facilitating the implementation and monitoring of specific treatments such as Xtandi®/Zytiga® 535, followed by Taxolere® 540 if necessary, followed by Cabazitaxel® 545 if necessary.

For example, at 502, the treatment assistant logic section 113 of the disease and disorder treatment device 103 can automatically educate the patient at 504 by sending educational information that is tailored to the specific characteristics of the lymph node and/or soft tissue therapy 340 to the smart mobile device 105 for display on the touch-sensitive screen 121. At 506, the treatment assistant logic section 113 of the disease and disorder treatment device 103 can automatically monitor the lymph node and/or soft tissue therapy 340 by receiving feedback and other responses of the patient from the smart mobile device 105. At 508, the treatment assistant logic section 113 of the disease and disorder treatment device 103 can automatically intervene when the patient experiences symptoms or other adverse effects during the treatment. The treatment assistant logic section 113 can assist the patient at each step during the lymph node and/or soft tissue therapy 340, such as by educating, monitoring patient condition, facilitating new prescriptions, and intervening in the therapy when necessary to improve the chances that the patient survives.

Figure 6:
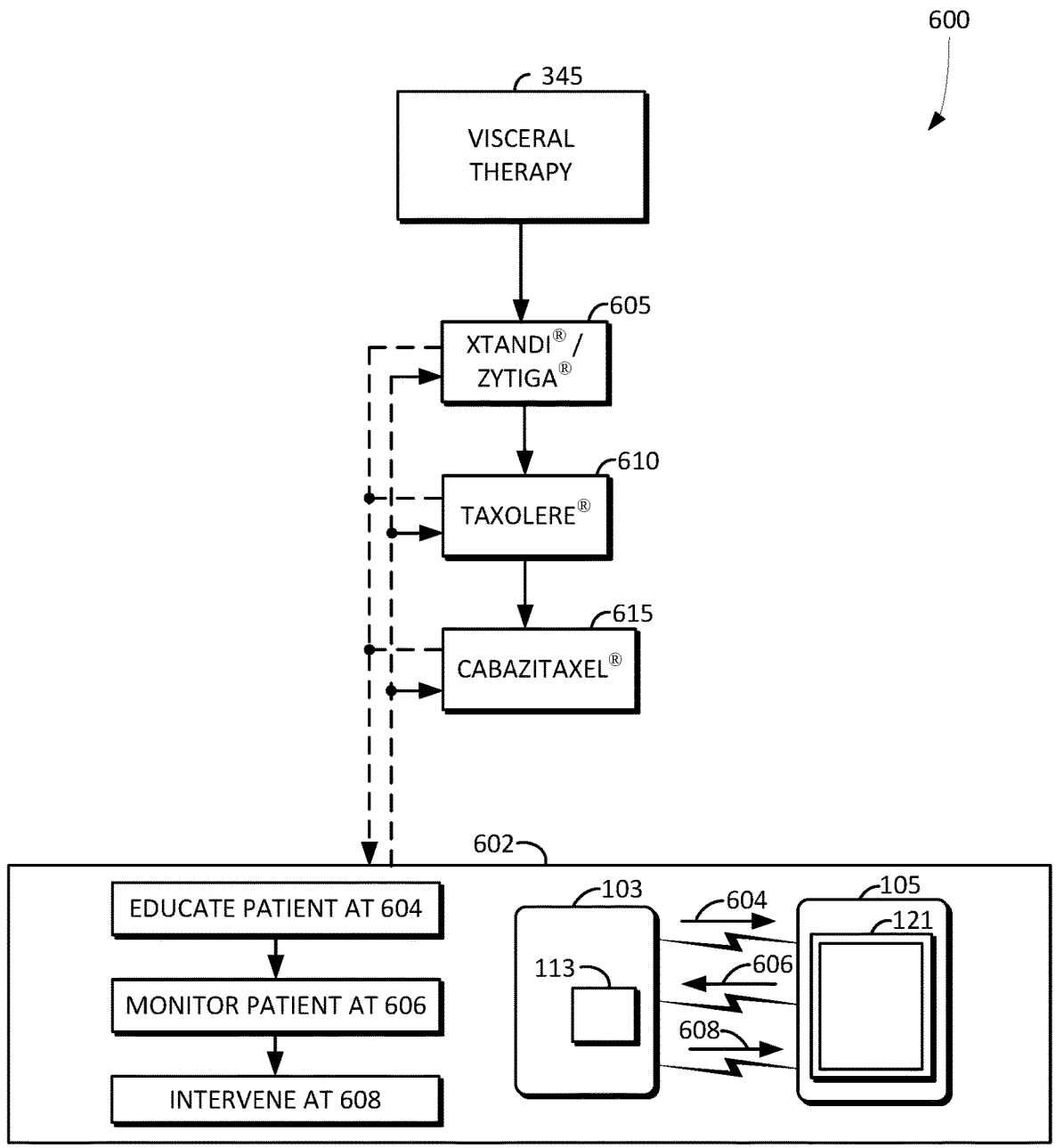
FIG. 6 illustrates a block and flow diagram showing an interactive treatment assistance technique related to visceral therapy in accordance with various embodiments of the present inventive concept.

FIG. 6 illustrates a block and flow diagram 600 showing an interactive treatment assistance technique related to visceral therapy in accordance with various embodiments of the present inventive concept. At 345, visceral therapy begins. Depending on specific characteristics associated with the form of prostate cancer that the patient might be experiencing, the treatment assistant logic section 113 of the disease and disorder treatment device 103 can automatically tailor the electronic pathway for educating, monitoring, and intervening on behalf of the patient. At 605, the treatment assistant logic section 113 of the disease and disorder treatment device 103 can automatically assist in the treatment by facilitating the implementation and monitoring of specific treatments such as Xtandi®/Zytiga® 605, followed by Taxolere® 610 if necessary, followed by Cabazitaxel® 615 if necessary.

For example, at 602, the treatment assistant logic section 113 of the disease and disorder treatment device 103 can automatically educate the patient at 604 by sending educational information that is tailored to the specific characteristics of the visceral therapy 345 to the smart mobile device 105 for display on the touch-sensitive screen 121. At 606, the treatment assistant logic section 113 of the disease and disorder treatment device 103 can automatically monitor the visceral therapy 345 by receiving feedback and other responses of the patient from the smart mobile device 105. At 608, the treatment assistant logic section 113 of the disease and disorder treatment device 103 can automatically intervene when the patient experiences symptoms or other adverse effects during the treatment. The treatment assistant logic section 113 can assist the patient at each step during the visceral therapy 345, such as by educating, monitoring patient condition, facilitating new prescriptions, and intervening in the therapy when necessary to improve the chances that the patient survives.

Figure 7:
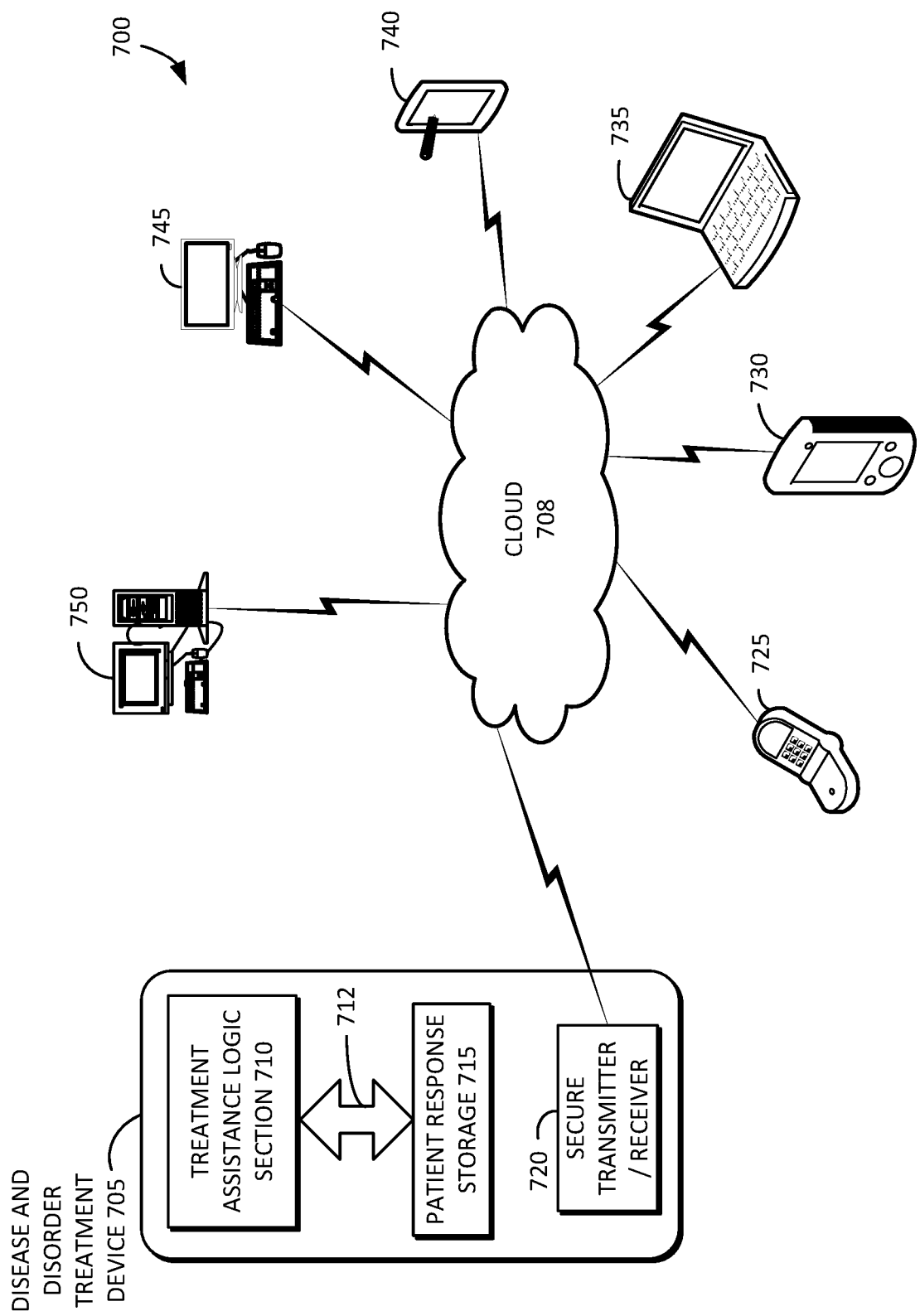
FIG. 7 illustrates a system for interactive treatment assistance for benign prostate hyperplasia and advanced prostate cancer in accordance with various embodiments of the present inventive concept.

FIG. 7 illustrates a system for interactive pre-anesthetic screening in accordance with various embodiments of the present inventive concept. The system 700 can include a disease and disorder treatment device 705 (e.g., 103). The disease and disorder treatment device 705 can include a treatment assistance logic section 710 (e.g., 113). The treatment assistance logic section 710 can process and cause the information described in the various electronic pathways and phases discussed above to be displayed on an electronic display. For example, an electronic display of a phone 725, smart phone 730, laptop computer 735, tablet 740, computer terminal 745, and/or computer workstation 750 can display the information caused to be displayed by the treatment assistance logic section 710. The information caused to be displayed by the treatment assistance logic section 710 can be transmitted via the cloud 708.

The disease and disorder treatment device 705 can include a bus 712 and a patient response storage section 715 (e.g., 117). The treatment assistance logic section 710 can provide a user interface with the user patient via the cloud 708. The treatment assistance logic section 710 can automatically receive user patient affirmations and other responses, and store such response information in the patient response storage section 715 via the bus 712. The disease and disorder treatment device 705 can include a secure transmitter/receiver 720 for securely transmitting and receiving information to and from the user patient via the cloud 708.

Embodiments are described herein, and illustrated in the drawings, in terms of functional blocks, units and/or modules. Those skilled in the art will appreciate that these blocks, units and/or modules can be physically implemented by electronic (or optical) circuits such as logic circuits, discrete components, microprocessors, hard-wired circuits, memory elements, wiring connections, and the like, which may be formed using semiconductor-based fabrication techniques or other manufacturing technologies. In the case of the blocks, units and/or modules being implemented by microprocessors or similar, they may be programmed using software (e.g., microcode) to perform various functions discussed herein and may optionally be driven by firmware and/or software. Alternatively, each block, unit and/or module may be implemented by dedicated hardware, or as a combination of dedicated hardware to perform some functions and a processor (e.g., one or more programmed microprocessors and associated circuitry) to perform other functions. Also, each block, unit and/or module of the embodiments may be physically separated into two or more interacting and discrete blocks, units and/or modules without departing from the scope of the inventive concepts. Further, the blocks, units and/or modules of the embodiments may be physically combined into more complex blocks, units and/or modules without departing from the scope of the inventive concepts.

Some embodiments include a computer-implemented method for providing interactive electronic treatment assistance for a benign prostatic hyperplasia (BPH) condition. The method can include automatically sending, by a disease and disorder treatment device, an electronic pathway sign-up link to a smart mobile device. The method can include receiving, by the disease and disorder treatment device, sign-up information from the smart mobile device. The method can include automatically sending, by the disease and disorder treatment device, a series of educational slides about the BPH condition to the smart mobile device. The method can include presenting, by the smart mobile device, the series of educational slides. The method can include automatically sending, by the disease and disorder treatment device, a reminder message regarding aspects that are important for improving the BPH condition, to the smart mobile device. The method can include automatically sending, by the disease and disorder treatment device, one or more educational links about the BPH condition, to the smart mobile device. The method can include automatically sending, by the disease and disorder treatment device, a plurality of inquiries about the BPH condition, to the smart mobile device. The method can include automatically receiving, by the disease and disorder treatment device, a plurality of patient responses to the plurality of inquiries about the BPH condition, from the smart mobile device. The method can include automatically processing, by the disease and disorder treatment device, the plurality of patient responses. The method can include automatically storing, by the disease and disorder treatment device, the plurality of patient responses.

In some embodiments, the method can include automatically sending the reminder a first predefined number of days after receiving the sign-up information to the smart mobile device, wherein the reminder includes information about the importance of at least one of avoiding dietary irritants or maintaining proper urinary habits. The method can include automatically sending, by the disease and disorder treatment device, a first inquiry message a second predefined number of days after receiving the sign-up information to the smart mobile device, wherein the first inquiry message regards whether symptoms associated with the BPH condition have satisfactorily subsided.

The method can include automatically receiving, by the disease and disorder treatment device, a patient response regarding whether the symptoms have satisfactorily subsided from the smart mobile device. The method can include automatically processing, by the disease and disorder treatment device, the patient response regarding whether the symptoms have satisfactorily subsided.

The method can include, responsive to the patient response regarding whether the symptoms have satisfactorily subsided being affirmative, automatically sending a first congratulatory message to the smart mobile device. The method can include responsive to the patient response regarding whether the symptoms have satisfactorily subsided not being affirmative, automatically sending an exhortation message to the smart mobile device.

In some embodiments, the method can include automatically sending, by the disease and disorder treatment device, a second inquiry message a third predefined number of days after receiving the sign-up information to the smart mobile device, wherein the second inquiry message regards whether the symptoms have satisfactorily subsided. The method can include automatically receiving, by the disease and disorder treatment device, a patient response regarding whether the symptoms have satisfactorily subsided. The method can include automatically processing, by the disease and disorder treatment device, the patient response regarding whether the symptoms have satisfactorily subsided.

In some embodiments, the method can include, responsive to the patient response regarding whether the symptoms have satisfactorily subsided being affirmative, automatically sending a second congratulatory message to the smart mobile device. The method can include responsive to the patient response regarding whether the symptoms have satisfactorily subsided not being affirmative, automatically sending, by the disease and disorder treatment device, a third inquiry message regarding whether a patient would like to try a medication. The method can include automatically receiving, by the disease and disorder treatment device, a patient response regarding whether the patient would like to try the medication from the smart mobile device. The method can include automatically processing, by the disease and disorder treatment device, the patient response regarding whether the patient would like to try the medication. The method can include, responsive to the patient response regarding whether the patient would like to try the medication not being affirmative, automatically sending a fourth inquiry message regarding whether the patient would like an in-person appointment with a health care provider to discuss the medication further. The method can include automatically receiving, by the disease and disorder treatment device, a patient response regarding whether the patient would like the in-person appointment with the health care provider to discuss the medication further. The method can include automatically processing, by the disease and disorder treatment device, the patient response regarding whether the patient would like the in-person appointment with the health care provider to discuss the medication further.

In some embodiments, the method can include, responsive to the patient response regarding whether the patient would like the in-person appointment with the health care provider being affirmative, facilitating, by the disease and disorder treatment device, scheduling of the in-person appointment with the health care provider.

In some embodiments, the method can include, responsive to the patient response regarding whether the patient would like to try the medication being affirmative, automatically sending a reminder message regarding filling a prescription given to the patient at a last office visit with the health care provider.

In some embodiments, the method can include automatically sending, by the disease and disorder treatment device, a fifth inquiry message a fourth predefined number of days after receiving the sign-up information to the smart mobile device, wherein the fifth inquiry message regards whether the symptoms associated with the BPH condition have satisfactorily subsided. The method can include automatically receiving, by the disease and disorder treatment device, a patient response regarding whether the symptoms have satisfactorily subsided. The method can include automatically processing, by the disease and disorder treatment device, the patient response regarding whether the symptoms have satisfactorily subsided.

In some embodiments, the method can include, responsive to the patient response regarding whether the symptoms have satisfactorily subsided being affirmative, automatically sending a third congratulatory message to the smart mobile device. The method can include, responsive to the patient response regarding whether the symptoms have satisfactorily subsided not being affirmative, automatically sending, by the disease and disorder treatment device, a sixth inquiry message regarding whether the patient would like to try a different medication. The method can include automatically receiving, by the disease and disorder treatment device, a patient response regarding whether the patient would like to try the different medication from the smart mobile device. The method can include automatically processing, by the disease and disorder treatment device, the patient response regarding whether the patient would like to try the different medication. The method can include, responsive to the patient response regarding whether the patient would like to try the different medication not being affirmative, automatically sending a seventh inquiry message regarding whether the patient would like the in-person appointment with the health care provider to discuss further options. The method can include automatically receiving, by the disease and disorder treatment device, a patient response regarding whether the patient would like the in-person appointment with the health care provider to discuss the further options. The method can include automatically processing, by the disease and disorder treatment device, the patient response regarding whether the patient would like the in-person appointment with the health care provider to discuss the further options.

In some embodiments, the method can include automatically sending, by the disease and disorder treatment device, an eighth inquiry message a fifth predefined number of days after receiving the sign-up information to the smart mobile device, wherein the eighth inquiry message regards whether the symptoms associated with the BPH condition have satisfactorily subsided. The method can include automatically receiving, by the disease and disorder treatment device, a patient response regarding whether the symptoms have satisfactorily subsided from the smart mobile device. The method can include automatically processing, by the disease and disorder treatment device, the patient response regarding whether the symptoms have satisfactorily subsided.

In some embodiments, the method can include, responsive to the patient response regarding whether the symptoms have satisfactorily subsided being affirmative, automatically sending a fourth congratulatory message to the smart mobile device. The method can include responsive to the patient response regarding whether the symptoms have satisfactorily subsided not being affirmative, automatically sending, by the disease and disorder treatment device, a ninth inquiry message regarding whether the patient would like to schedule an appointment to discuss potential testing and other treatments to the smart mobile device.

In some embodiments, the method can include automatically sending, by the disease and disorder treatment device, a first informational message including educational material pertaining to holmium laser eunucleation of the prostate to the smart mobile device. The method can include automatically sending, by the disease and disorder treatment device, a second informational message including educational material pertaining to holmium laser ablation of the prostate to the smart mobile device. The method can include automatically sending, by the disease and disorder treatment device, a third informational message including educational material pertaining to transurethral electroevaporation of the prostate to the smart mobile device. The method can include automatically sending, by the disease and disorder treatment device, a fourth informational message including educational material pertaining to transurethral microwave thermotherapy to the smart mobile device. The method can include automatically sending, by the disease and disorder treatment device, a fifth informational message including educational material pertaining to transurethral needle ablation to the smart mobile device. The method can include automatically sending, by the disease and disorder treatment device, a sixth informational message including educational material pertaining to photoselective vaporization to the smart mobile device.

In some embodiments, the method can include automatically sending, by the disease and disorder treatment device, a seventh informational message including educational material pertaining to transurethral resection of the prostate to the smart mobile device. The method can include automatically sending, by the disease and disorder treatment device, a eighth informational message including educational material pertaining to Rezum therapy to the smart mobile device.

In some embodiments, the first predefined number of days is 2, the second predefined number of days is 7 days, the third predefined number of days is 14 days, the fourth predefined number of days is 28 days, and the fifth predefined number of days is 42 days.

Some embodiments include a computer-implemented method for providing interactive electronic treatment assistance for an advanced prostate cancer condition. The method can include automatically sending, by a disease and disorder treatment device, an electronic pathway sign-up link to a smart mobile device. The method can include receiving, by the disease and disorder treatment device, sign-up information from the smart mobile device. The method can include automatically sending, by the disease and disorder treatment device, a series of educational slides about the advanced prostate cancer condition to the smart mobile device. The method can include presenting, by the smart mobile device, the series of educational slides. The method can include automatically sending, by the disease and disorder treatment device, a plurality of inquiries about the advanced prostate cancer condition, to the smart mobile device. The method can include receiving, by the disease and disorder treatment device, a plurality of patient responses to the plurality of inquiries about the advanced prostate cancer condition, from the smart mobile device. The method can include automatically processing, by the disease and disorder treatment device, the plurality of patient responses. The method can include automatically storing, by the disease and disorder treatment device, the plurality of patient responses.

In some embodiments, the method can include automatically providing, by the disease and disorder treatment device, patient education about androgen deprivation therapy (ADT) to the smart mobile device. The method can include automatically monitoring, by the disease and disorder treatment device, a patient having the advanced prostate cancer condition during the ADT therapy using the smart mobile device. The method can include automatically intervening, by the disease and disorder treatment device, with the ADT therapy using the smart mobile device.

In some embodiments, the method can include automatically providing, by the disease and disorder treatment device, patient education about bone therapy to the smart mobile device. The method can include automatically monitoring, by the disease and disorder treatment device, a patient having the advanced prostate cancer condition during the bone therapy using the smart mobile device. The method can include automatically intervening, by the disease and disorder treatment device, with the bone therapy using the smart mobile device.

In some embodiments, the method can include automatically providing, by the disease and disorder treatment device, patient education about lymph node therapy to the smart mobile device. The method can include automatically monitoring, by the disease and disorder treatment device, a patient having the advanced prostate cancer condition during the lymph node therapy using the smart mobile device. The method can include automatically intervening, by the disease and disorder treatment device, with the lymph node therapy using the smart mobile device.

In some embodiments, the method can include automatically providing, by the disease and disorder treatment device, patient education about visceral therapy to the smart mobile device. The method can include automatically monitoring, by the disease and disorder treatment device, a patient having the advanced prostate cancer condition during the visceral therapy using the smart mobile device. The method can include automatically intervening, by the disease and disorder treatment device, with the visceral therapy using the smart mobile device.

The following discussion is intended to provide a brief, general description of a suitable machine or machines in which certain aspects of the inventive concept can be implemented. Typically, the machine or machines include a system bus to which is attached processors, memory, e.g., random access memory (RAM), read-only memory (ROM), or other state preserving medium, storage devices, a video interface, and input/output interface ports. The machine or machines can be controlled, at least in part, by input from conventional input devices, such as keyboards, mice, etc., as well as by directives received from another machine, interaction with a virtual reality (VR) environment, biometric feedback, or other input signal. As used herein, the term "machine" is intended to broadly encompass a single machine, a virtual machine, or a system of communicatively coupled machines, virtual machines, or devices operating together. Exemplary machines include computing devices such as personal computers, workstations, servers, portable computers, handheld devices, telephones, tablets, etc., as well as transportation devices, such as private or public transportation, e.g., automobiles, trains, cabs, etc.

The machine or machines can include embedded controllers, such as programmable or non-programmable logic devices or arrays, Application Specific Integrated Circuits (ASICs), embedded computers, smart cards, and the like. The machine or machines can utilize one or more connections to one or more remote machines, such as through a network interface, modem, or other communicative coupling. Machines can be interconnected by way of a physical and/or logical network, such as an intranet, the Internet, local area networks, wide area networks, etc. One skilled in the art will appreciate that network communication can utilize various wired and/or wireless short range or long range carriers and protocols, including radio frequency (RF), satellite, microwave, Institute of Electrical and Electronics Engineers (IEEE) 545.11, Bluetooth®, optical, infrared, cable, laser, etc.

Embodiments of the inventive concept can be described by reference to or in conjunction with associated data including functions, procedures, data structures, application programs, etc. which when accessed by a machine results in the machine performing tasks or defining abstract data types or low-level hardware contexts. Associated data can be stored in, for example, the volatile and/or non-volatile memory, e.g., RAM, ROM, etc., or in other storage devices and their associated storage media, including hard-drives, floppy-disks, optical storage, tapes, flash memory, memory sticks, digital video disks, biological storage, etc. Associated data can be delivered over transmission environments, including the physical and/or logical network, in the form of packets, serial data, parallel data, propagated signals, etc., and can be used in a compressed or encrypted format. Associated data can be used in a distributed environment, and stored locally and/or remotely for machine access.

Having described and illustrated the principles of the inventive concept with reference to illustrated embodiments, it will be recognized that the illustrated embodiments can be modified in arrangement and detail without departing from such principles, and can be combined in any desired manner And although the foregoing discussion has focused on particular embodiments, other configurations are contemplated. In particular, even though expressions such as "according to an embodiment of the invention" or the like are used herein, these phrases are meant to generally reference embodiment possibilities, and are not intended to limit the inventive concept to particular embodiment configurations. As used herein, these terms can reference the same or different embodiments that are combinable into other embodiments.

Embodiments of the invention may include a non-transitory machine-readable medium comprising instructions executable by one or more processors, the instructions comprising instructions to perform the elements of the embodiments as described herein.

Consequently, in view of the wide variety of permutations to the embodiments described herein, this detailed description and accompanying material is intended to be illustrative only, and should not be taken as limiting the scope of the inventive concept. What is claimed as the invention, therefore, is all such modifications as may come within the scope and spirit of the following claims and equivalents thereto.

The invention claimed is:

1. A computer-implemented method for providing interactive electronic treatment assistance for a benign prostatic hyperplasia (BPH) condition, the method comprising:

automatically sending, by a disease and disorder treatment device, an electronic pathway sign-up link to a smart mobile device;

receiving, by the disease and disorder treatment device, sign-up information from the smart mobile device;

automatically sending, by the disease and disorder treatment device, a series of educational slides about the BPH condition to the smart mobile device;

presenting, by the smart mobile device, the series of educational slides;

automatically sending, by the disease and disorder treatment device, a reminder message regarding aspects that are important for improving the BPH condition, to the smart mobile device;

automatically sending, by the disease and disorder treatment device, one or more educational links about the BPH condition, to the smart mobile device;

automatically sending, by the disease and disorder treatment device, a plurality of inquiries about the BPH condition, to the smart mobile device;

automatically receiving, by the disease and disorder treatment device, a plurality of patient responses to the plurality of inquiries about the BPH condition, from the smart mobile device;

automatically processing, by the disease and disorder treatment device, the plurality of patient responses; and automatically storing, by the disease and disorder treatment device, the plurality of patient responses.

2. The computer-implemented method of claim 1, further comprising:

automatically sending the reminder a first predefined number of days after receiving the sign-up information to the smart mobile device, wherein the reminder includes information about the importance of at least one of avoiding dietary irritants or maintaining proper urinary habits;

automatically sending, by the disease and disorder treatment device, a first inquiry message a second predefined number of days after receiving the sign-up information to the smart mobile device, wherein the first inquiry message regards whether symptoms associated with the BPH condition have satisfactorily subsided;

automatically receiving, by the disease and disorder treatment device, a patient response regarding whether the symptoms have satisfactorily subsided from the smart mobile device;

automatically processing, by the disease and disorder treatment device, the patient response regarding whether the symptoms have satisfactorily subsided;

responsive to the patient response regarding whether the symptoms have satisfactorily subsided being affirmative, automatically sending a first congratulatory message to the smart mobile device; and responsive to the patient response regarding whether the symptoms have satisfactorily subsided not being affirmative, automatically sending an exhortation message to the smart mobile device.

3. The computer-implemented method of claim 2, further comprising:

automatically sending, by the disease and disorder treatment device, a second inquiry message a third predefined number of days after receiving the sign-up information to the smart mobile device, wherein the second inquiry message regards whether the symptoms have satisfactorily subsided;

automatically receiving, by the disease and disorder treatment device, a patient response regarding whether the symptoms have satisfactorily subsided; and automatically processing, by the disease and disorder treatment device, the patient response regarding whether the symptoms have satisfactorily subsided.

4. The computer-implemented method of claim 3, further comprising:

responsive to the patient response regarding whether the symptoms have satisfactorily subsided being affirmative, automatically sending a second congratulatory message to the smart mobile device;

responsive to the patient response regarding whether the symptoms have satisfactorily subsided not being affirmative, automatically sending, by the disease and disorder treatment device, a third inquiry message regarding whether a patient would like to try a medication;

automatically receiving, by the disease and disorder treatment device, a patient response regarding whether the patient would like to try the medication from the smart mobile device;

automatically processing, by the disease and disorder treatment device, the patient response regarding whether the patient would like to try the medication;

responsive to the patient response regarding whether the patient would like to try the medication not being affirmative, automatically sending a fourth inquiry message regarding whether the patient would like an in-person appointment with a health care provider to discuss the medication further;

automatically receiving, by the disease and disorder treatment device, a patient response regarding whether the patient would like the in-person appointment with the health care provider to discuss the medication further; and automatically processing, by the disease and disorder treatment device, the patient response regarding whether the patient would like the in-person appointment with the health care provider to discuss the medication further.

5. The computer-implemented method of claim 4, further comprising:

responsive to the patient response regarding whether the patient would like the in-person appointment with the health care provider being affirmative, facilitating, by the disease and disorder treatment device, scheduling of the in-person appointment with the health care provider.

6. The computer-implemented method of claim 5, further comprising:

responsive to the patient response regarding whether the patient would like to try the medication being affirmative, automatically sending a reminder message regarding filling a prescription given to the patient at a last office visit with the health care provider.

7. The computer-implemented method of claim 6, further comprising:

automatically sending, by the disease and disorder treatment device, a fifth inquiry message a fourth predefined number of days after receiving the sign-up information to the smart mobile device, wherein the fifth inquiry message regards whether the symptoms associated with the BPH condition have satisfactorily subsided;

automatically receiving, by the disease and disorder treatment device, a patient response regarding whether the symptoms have satisfactorily subsided; and automatically processing, by the disease and disorder treatment device, the patient response regarding whether the symptoms have satisfactorily subsided.

8. The computer-implemented method of claim 7, further comprising:

responsive to the patient response regarding whether the symptoms have satisfactorily subsided being affirmative, automatically sending a third congratulatory message to the smart mobile device;

responsive to the patient response regarding whether the symptoms have satisfactorily subsided not being affirmative, automatically sending, by the disease and disorder treatment device, a sixth inquiry message regarding whether the patient would like to try a different medication;

automatically receiving, by the disease and disorder treatment device, a patient response regarding whether the patient would like to try the different medication from the smart mobile device;

automatically processing, by the disease and disorder treatment device, the patient response regarding whether the patient would like to try the different medication;

responsive to the patient response regarding whether the patient would like to try the different medication not being affirmative, automatically sending a seventh inquiry message regarding whether the patient would like the in-person appointment with the health care provider to discuss further options;

automatically receiving, by the disease and disorder treatment device, a patient response regarding whether the patient would like the in-person appointment with the health care provider to discuss the further options; and automatically processing, by the disease and disorder treatment device, the patient response regarding whether the patient would like the in-person appointment with the health care provider to discuss the further options.

9. The computer-implemented method of claim 8, further comprising:

automatically sending, by the disease and disorder treatment device, an eighth inquiry message a fifth predefined number of days after receiving the sign-up information to the smart mobile device, wherein the eighth inquiry message regards whether the symptoms associated with the BPH condition have satisfactorily subsided;

automatically receiving, by the disease and disorder treatment device, a patient response regarding whether the symptoms have satisfactorily subsided from the smart mobile device; and automatically processing, by the disease and disorder treatment device, the patient response regarding whether the symptoms have satisfactorily subsided.

10. The computer-implemented method of claim 9, further comprising:

responsive to the patient response regarding whether the symptoms have satisfactorily subsided being affirmative, automatically sending a fourth congratulatory message to the smart mobile device; and responsive to the patient response regarding whether the symptoms have satisfactorily subsided not being affirmative, automatically sending, by the disease and disorder treatment device, a ninth inquiry message regarding whether the patient would like to schedule an appointment to discuss potential testing and other treatments to the smart mobile device.

11. The computer-implemented method of claim 10, further comprising:

automatically sending, by the disease and disorder treatment device, a first informational message including educational material pertaining to holmium laser eunucleation of the prostate to the smart mobile device;

automatically sending, by the disease and disorder treatment device, a second informational message including educational material pertaining to holmium laser ablation of the prostate to the smart mobile device;

automatically sending, by the disease and disorder treatment device, a third informational message including educational material pertaining to transurethral electroevaporation of the prostate to the smart mobile device;

automatically sending, by the disease and disorder treatment device, a fourth informational message including educational material pertaining to transurethral microwave thermotherapy to the smart mobile device;

automatically sending, by the disease and disorder treatment device, a fifth informational message including educational material pertaining to transurethral needle ablation to the smart mobile device; and automatically sending, by the disease and disorder treatment device, a sixth informational message including educational material pertaining to photoselective vaporization to the smart mobile device.

12. The computer-implemented method of claim 11, further comprising:

automatically sending, by the disease and disorder treatment device, a seventh informational message including educational material pertaining to transurethral resection of the prostate to the smart mobile device; and automatically sending, by the disease and disorder treatment device, a eighth informational message including educational material pertaining to Rezum therapy to the smart mobile device.

13. The computer-implemented method of claim 12, wherein:

the first predefined number of days is 2;
the second predefined number of days is 7 days;
the third predefined number of days is 14 days;
the fourth predefined number of days is 28 days; and
the fifth predefined number of days is 42 days.

* * * * *